US010898701B2

(12) United States Patent
Boone

(10) Patent No.: US 10,898,701 B2
(45) Date of Patent: Jan. 26, 2021

(54) DEVICE FOR DELIVERING MEDICATION

(71) Applicant: AJB LLC, Bloomington, MN (US)

(72) Inventor: John L. Boone, Bloomington, MN (US)

(73) Assignee: AJB LLC, Bloomington, MN (US)

(*) Notice: Subject to any disclaimer, the term of this patent is extended or adjusted under 35 U.S.C. 154(b) by 79 days.

(21) Appl. No.: 15/952,014

(22) Filed: Apr. 12, 2018

(65) Prior Publication Data
US 2018/0296812 A1 Oct. 18, 2018

Related U.S. Application Data

(63) Continuation-in-part of application No. PCT/US2016/056603, filed on Oct. 12, 2016.

(60) Provisional application No. 62/574,227, filed on Oct. 19, 2017.

(51) Int. Cl.
A61M 31/00 (2006.01)
A61F 11/00 (2006.01)

(52) U.S. Cl.
CPC ............. A61M 31/00 (2013.01); A61F 11/00 (2013.01); A61M 2205/3379 (2013.01); A61M 2205/583 (2013.01); A61M 2210/0662 (2013.01)

(58) Field of Classification Search
CPC .......... A61M 31/00; A61M 2210/0662; A61M 3/02; A61M 3/0279; A61F 11/00; A61F 11/006
See application file for complete search history.

(56) References Cited

U.S. PATENT DOCUMENTS

| 2,719,523 A | 10/1955 | Von |
| 3,430,817 A | 3/1969 | Falkenberg |
| 3,834,241 A | 9/1974 | Sarver et al. |
| 3,894,539 A * | 7/1975 | Tallent ................ A61M 31/00 604/57 |
| 4,212,204 A | 7/1980 | St. Amand |
| 4,779,768 A | 10/1988 | St. Amand |
| 4,820,259 A * | 4/1989 | Stevens ................ A61F 11/00 604/1 |
| 5,299,581 A | 4/1994 | Donnell et al. |
| 5,772,665 A * | 6/1998 | Glad ..................... A61M 5/284 604/82 |
| 5,775,546 A | 7/1998 | Buehler |

(Continued)

FOREIGN PATENT DOCUMENTS

EP 0243261 10/1987
WO 2017066297 4/2017

OTHER PUBLICATIONS

"International Preliminary Report on Patentability," for PCT Application No. PCT/US2016/056603 dated Apr. 26, 2018 (7 pages).

(Continued)

Primary Examiner — Nathan R Price
Assistant Examiner — Melissa A Snyder
(74) Attorney, Agent, or Firm — Pauly, DeVries Smith & Deffner LLC

(57) ABSTRACT

A device for the dispensing of liquids is disclosed. In an embodiment the device comprises a first hollow bulb coupled to a second hollow bulb, wherein the first hollow bulb is compressible; and a separator element disposed between the first hollow bulb and the second hollow bulb, wherein the separator element defines a passage; wherein the second hollow bulb defines an opening.

14 Claims, 32 Drawing Sheets

(56) References Cited

U.S. PATENT DOCUMENTS

| | | | | |
|---|---|---|---|---|
| 5,848,993 | A | * | 12/1998 | Tanhehco ............. A61M 1/0011 604/217 |
| 6,537,260 | B1 | * | 3/2003 | Lamb ................. A61M 3/0262 604/279 |
| 2001/0042572 | A1 | * | 11/2001 | Faughey ............... B01L 3/0282 141/24 |
| 2003/0220585 | A1 | | 11/2003 | Hissong |
| 2006/0253087 | A1 | * | 11/2006 | Vlodaver ................ A61F 11/00 604/275 |
| 2011/0166523 | A1 | * | 7/2011 | Javer ..................... A61H 35/04 604/151 |
| 2014/0260698 | A1 | | 9/2014 | Wu |
| 2015/0142029 | A1 | * | 5/2015 | Fahn .................... A61F 11/006 606/162 |
| 2015/0259188 | A1 | | 9/2015 | Smith et al. |

OTHER PUBLICATIONS

"International Search Report and Written Opinion," for PCT Application No. PCT/US2016/056603 dated Feb. 8, 2017 (10 pages).
Extended European Search Report for European Patent Application No. 16856098.5 dated May 15, 2019 (7 pages).
Response to Communication Pursuant to Rules 161(1) and 162 EPC for European Patent Application No. 16856098.5 filed Nov. 29, 2018 (4 pages).
Response to Communication Pursuant to Rules 70(2) and 70a(2) EPC for European Patent Application No. 16856098.5 filed Dec. 13, 2019 (24 pages).

* cited by examiner

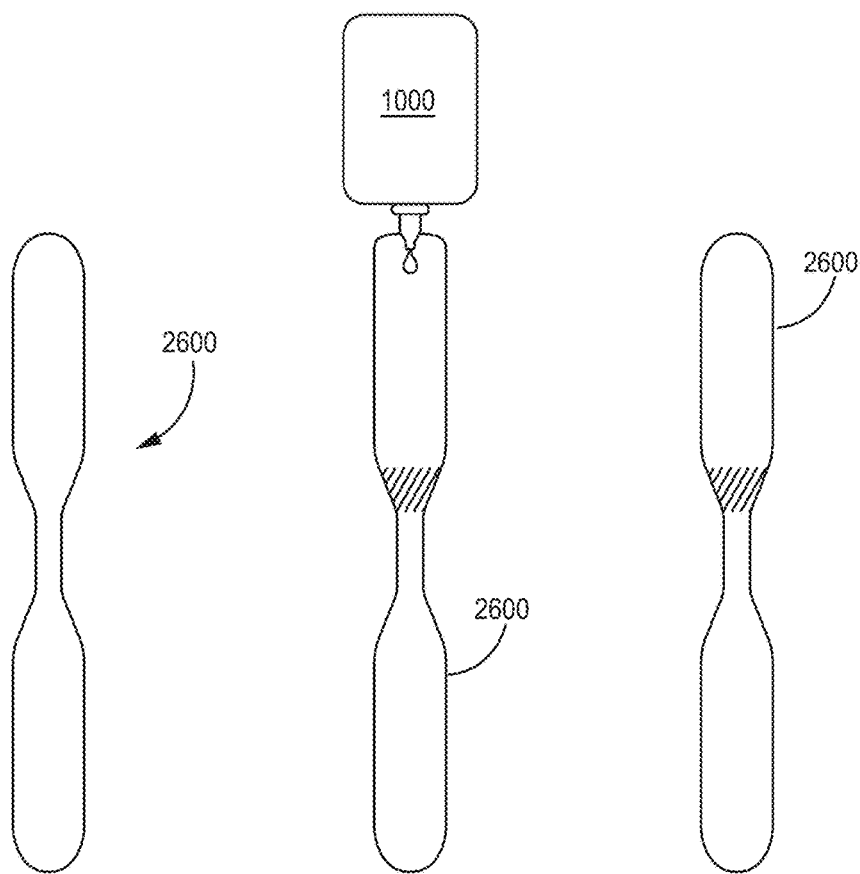
FIG. 26　　FIG. 27　　FIG. 28
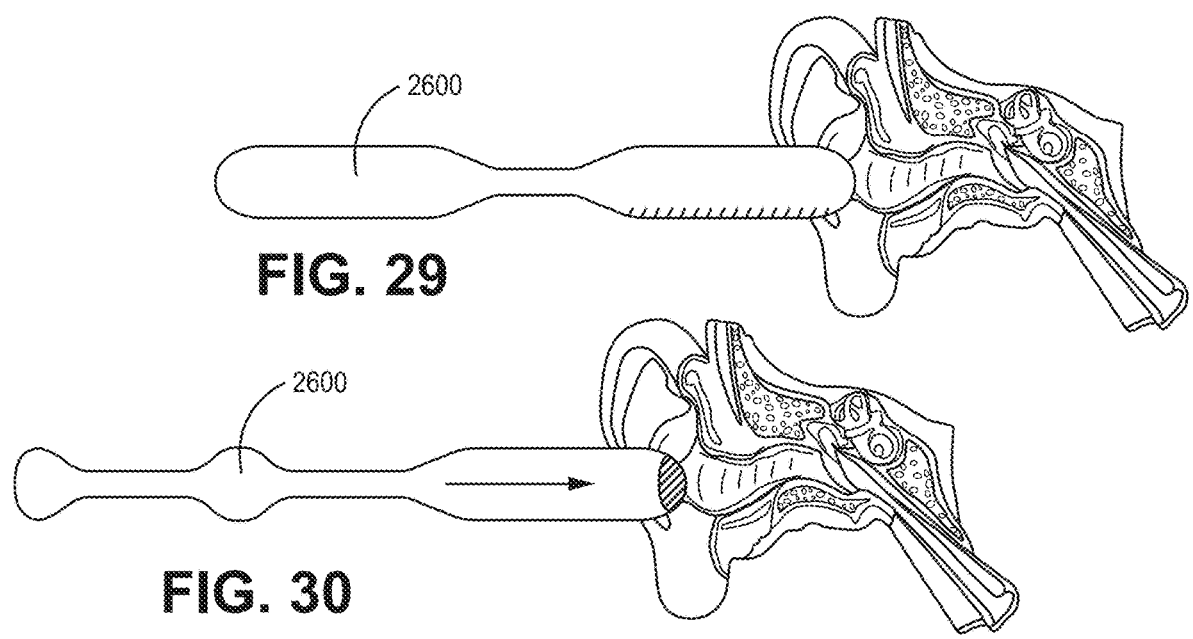
FIG. 29
FIG. 30

DEVICE FOR DELIVERING MEDICATION

FIELD OF THE TECHNOLOGY

The present application relates to a device for the dispensing of liquids. More specifically, the present application relates to a device for the dispensing of liquids into a patient's ear.

BACKGROUND

Liquid medications are frequently administered to a patient through drops. The drops can be applied to a target location, such as the patient's eyes or ears, through the use of a dropper or directly from bottles with dispensing tips. Current droppers that are commercially available can be inefficient at directing the liquid to the target location resulting in wasted medication, have increased costs, and decreased clinical efficacy. Current droppers also cause trauma to the ear canal in some circumstances.

Droppers currently available are frequently designed to be held in a vertical orientation with the opening facing downward. The liquid medication can drop from the dropper towards the target location, with the drops of medication are propelled by gravity. Relying on gravity to propel the drops can make it difficult for the drops to reach their target location. Relying on gravity often decreases efficacy and increases the number of drops needed to treat a condition—thus increasing cost.

Accordingly, there is a need for an apparatus and a method that results in a safe, more efficient use of the liquid medication and improves likelihood that the liquid medication reaches its target location, and improved clinical efficacy while decreasing cost.

SUMMARY

The present application is directed, in part, to a device for the dispensing of liquids, comprising a first hollow bulb, wherein the first hollow bulb is compressible; a second hollow bulb; and a hollow stem comprising a first end and a second end, wherein the first hollow bulb is coupled to the first end and the second hollow bulb is coupled to the second end; wherein the second hollow bulb defines an opening opposite from the hollow stem; wherein the first hollow bulb is in fluid communication with the second hollow bulb; and wherein the second end of the hollow stem terminates within the second hollow bulb.

The application is also directed to a device for the dispensing of liquids comprising a first hollow bulb coupled to a second hollow bulb, wherein the first hollow bulb is compressible; and a separator element disposed between the first hollow bulb and the second hollow bulb, wherein the separator element defines a passage; and wherein the second hollow bulb defines an opening.

The application is further directed to a method for delivering a liquid into a patient's ear, the device comprising: dispensing the liquid into the second hollow bulb of a device by inserting a tip of a bottle of liquid into an opening defined by the second hollow bulb; removing the tip of the bottle from the opening; aligning the second hollow bulb with a patient's ear; and projecting the liquid into the patient's ear by compressing a first hollow bulb of the device, wherein the first hollow bulb of the device is in fluid communication with the second hollow bulb through a hollow stem; wherein the hollow stem terminates within the second hollow bulb.

The present application is also directed to a device for the dispensing of liquids, comprising: a first hollow bulb, wherein the first hollow bulb is compressible; a second hollow bulb, the second hollow bulb having a volume less than the first hollow bulb and having a tapered configuration, the second hollow bulb comprising vents along its side an opening; wherein the first hollow bulb is coupled to the second hollow bulb via a conduit, the conduit integrally formed with the first hollow bulb and second hollow bulb; wherein the first hollow bulb is in fluid communication with the second hollow bulb along the coupling; wherein the second hollow bulb includes vents along its side.

In some implementations the second hollow bulb comprises volumetric indicia.

In some implementations the coupling comprises a flexible stem.

In some implementations wherein the opening is defined by a rounded surface of the second hollow bulb.

In some implementations the first hollow bulb, second hollow bulb, and the hollow stem comprise a transparent polymer.

In some implementations the first hollow bulb, second hollow bulb, and the hollow stem comprise polystyrene, polyethylene, polypropylene, polyvinyl chloride, SBS rubber, other rubbers, polyurethane, silicone rubber, and combinations thereof.

In some implementations the device is configured to discharge liquid from the second bulb through the opening.

In some implementations the first bulb, second bulb and stem are monolithic.

In some implementations the first bulb and the second bulb have circular cross-sections.

In some implementations the first bulb has a length substantially equal to the length of the second bulb.

In some implementations first bulb has a diameter of at least 1 mm and not more than 30 mm.

In some implementations the second bulb has a diameter of at least 1 mm and not more than 30 mm.

In some implementations the first bulb is substantially the same size as the second bulb.

The application is also directed to a device for the dispensing of liquids, the device comprising a first hollow bulb, wherein the first hollow bulb is compressible; a second hollow bulb; and a hollow stem comprising a first end and a second end, wherein the first hollow bulb is coupled to the first end and the second hollow bulb is coupled to the second end; wherein the second hollow bulb defines an opening opposite from the hollow stem; wherein the first hollow bulb is in fluid communication with the second hollow bulb; wherein the second end of the hollow stem terminates within the second hollow bulb.

In some implementations the second end of the hollow stem is tapered.

In some implementations the opening is a slit.

In some implementations the opening comprises two perpendicular slits.

In some implementations the second hollow bulb comprises volumetric indicia.

In some implementations the stem is flexible.

In some implementations wherein the opening is defined by a rounded surface of the second hollow bulb.

In some implementations the stem is enclosed within the first hollow bulb and the second hollow bulb.

In some implementations the first hollow bulb, second hollow bulb, and the hollow stem comprise a transparent polymer.

In some implementations the first hollow bulb, second hollow bulb, and the hollow stem comprise polystyrene, polyethylene, polypropylene, polyvinyl chloride, SBS rubber, other rubbers, polyurethane, silicone rubber, and combinations thereof.

In some implementations device is configured to discharge liquid from the second bulb through the opening.

The application is also directed to a device for the dispensing of liquids, comprising a first hollow bulb coupled to a second hollow bulb, wherein the first hollow bulb is compressible; and a separator element disposed between the first hollow bulb and the second hollow bulb, wherein the separator element defines a passage; wherein the second hollow bulb defines an opening.

In some implementations the separator element comprises a hollow shaft.

In some implementations least one end of the hollow shaft is tapered.

In some implementations the device has a total length of at least 1 cm and not more than 10 cm.

In some implementations the device has a consistent cross-section over at least 75% of the length of the device.

In some implementations the device has a circular cross-section over at least 75% of the length of the device.

In some implementations the first hollow bulb has the same volume as the second hollow bulb.

In some implementations the first hollow bulb has a larger volume than the second hollow bulb.

In some implementations the first hollow bulb is configured to be filled with air and the second hollow bulb is configured to be at least partially filled with a liquid.

In some implementations a distal end of the second hollow bulb is blunt.

The application is also directed to a method for delivering a liquid into a patient's ear, comprising: dispensing the liquid into the second hollow bulb of a device by inserting a tip of a bottle of liquid into an opening defined by the second hollow bulb; removing the tip of the bottle from the opening; aligning the second hollow bulb with a patient's ear; and projecting the liquid into the patient's ear by compressing a first hollow bulb of the device, wherein the first hollow bulb of the device is in fluid communication with the second hollow bulb through a hollow stem; wherein the hollow stem terminates within the second hollow bulb.

The application is also directed to a device for dispensing fluids, the device comprising: a compressible first hollow bulb; a second hollow bulb; a gap between the first hollow bulb and the second hollow bulb; and a stem coupling the first hollow bulb and the second hollow bulb, the stem providing fluid flow between the first hollow bulb and the second hollow bulb.

In some implementations the stem further comprises at least one support member spanning the gap between the first hollow bulb and the second hollow bulb.

In some implementations the stem flexibly couples the first hollow bulb and the second hollow bulb to allow the first hollow bulb and the second hollow bulb to move relative to one another.

Optionally In some implementations the device further comprises means for limiting fluid flow from the second hollow bulb into the first hollow bulb.

In some implementations the means for limiting fluid flow comprise an insert that narrows the inside diameter of the stem.

In some implementations the means for limiting fluid flow includes a valve.

In some implementations at least one support member spanning the gap between the first hollow bulb and the second hollow bulb.

In some implementations the support member limits the relative movement of the first hollow bulb and the second hollow bulb to one plane of motion.

This application is further directed to a device for dispensing fluids, the device comprising: a compressible first hollow bulb; a second hollow bulb having a bulb tip for dispensing fluid; and a groove along the surface of the second hollow bulb, the groove extending from the bulb tip.

In some implementations the groove is curved. In some implementations second hollow bulb further comprises an axis and the curve is at least partially helical around the axis.

A cap for dispensing liquids, the cap comprising, a bulb comprising a tapered portion; an inlet, an outlet, and flutes.

The disclosures further provide a device for dispensing fluids, which has a compressible first hollow bulb, a second hollow bulb, a gap between the first hollow bulb and the second hollow bulb, and a stem providing fluid flow between the first hollow bulb and the second hollow bulb. The stem may include a support member spanning the gap between the first hollow bulb and the second hollow bulb. The stem may be flexible, allowing the first hollow bulb and the second hollow bulb to move relative to one another. The movement may be limited to one plane of motion.

Another aspect provides a device for dispensing fluids, which has a compressible first hollow bulb, a second hollow bulb having a bulb tip for dispensing fluid, and a groove along the surface of the second hollow bulb, the groove extending from the bulb tip. The groove may be curved. Furthermore, the groove may be curved at least partially helically around the axis of the second hollow bulb.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present application is defined by the appended claims and their legal equivalents.

BRIEF DESCRIPTION OF THE FIGURES

The technology may be more completely understood relating to the following drawings, in which:

FIG. 26 is a front view of a device, according to an embodiment.

FIG. 27 is a front view of a device being filled, according to an embodiment.

FIG. 28 is a front view of a filled device, according to an embodiment.

FIG. 29 is a front view of a filled device aligned with a patient's ear, according to an embodiment.

FIG. 30 is a front view of a device aligned with a patient's ear, according to an embodiment.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The embodiments of the present technology described herein are not intended to be exhaustive or to limit the technology to the precise forms disclosed in the following detailed description. Rather, the embodiments are chosen and described so that others skilled in the art can appreciate and understand the principles and practices of the present technology.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

A device and method for the dispensing of liquids is disclosed herein. A device can refer to an apparatus for transferring or measuring out small quantities of liquid. The device and method can relate to the delivery of liquids to a patient's ear. In various embodiments disclosed herein, the liquid is a drug or medicine that is intended to be delivered into a patient's ear/ear canal/middle ear.

The device can include a first bulb or chamber and a second bulb or chamber. The first bulb can be configured to be empty or filled with ambient air. The second bulb can be configured to hold at least some liquid, such as a drug or medicine. The drug or medicine can be intended to be delivered to a location within a patient's ear. The second bulb can be configured so the tip protects the ear canal and achieves an air-tight seal. An air-tight seal, or substantially air-tight seal, helps the propulsion from the first bulb to drive the medicine into the ear canal and middle ear, increasing efficiency. Commonly such liquids are referred to as ear drops. The liquid can be delivered to a patient's ear to treat an infection, prevent an infection, or otherwise treat a problem at the patient's ear.

The first bulb can be compressed or deformed by a user, such as the patient, a doctor, a nurse or another medical professional. Compressing the first bulb can result in the liquid within the second bulb being propelled out of the second bulb through an opening and into the patient's ear/ear canal/middle ear.

Figure 1:
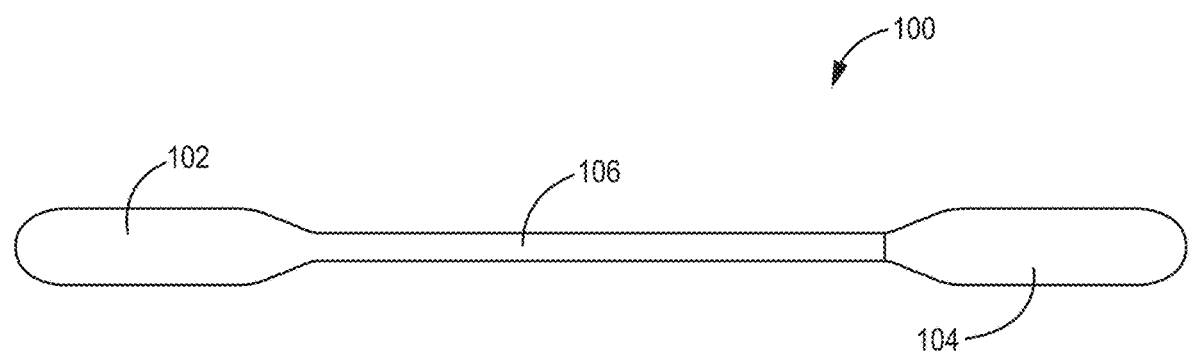
FIG. 1 is a front view of a device for dispensing medication, according to an embodiment.

In reference now to the figures, FIG. 1 shows a front view of a device 100, according to an embodiment. The device 100 can define a first bulb 102, a second bulb 104 and a stem 106. In various embodiments, the first bulb 102 can be hollow, such that first bulb 102 defines an internal cavity. The internal cavity of the first bulb 102 can be configured to hold air. In various embodiments, the second bulb 104 can be hollow, such that second bulb 104 defines an internal cavity. The internal cavity of the second bulb 104 can be configured to hold liquid and/or air. The internal cavity of the second bulb 104 can be configured to be at least partially filled with liquid.

In various embodiments, the stem 106 can be hollow, such that air from the first bulb 102 can travel through the stem 106 and into the second bulb 104. In various embodiments the stem 106 can have a circular cross-section. In various embodiments, the first bulb 102 and the second bulb 104 can have circular cross-sections.

The first bulb 102 and the second bulb 104 can be in fluid communication, such that gas/ambient air (liquid or gas) can travel from the first bulb 102 to the second bulb 104, such as through the stem 106. The first bulb 102 can be compressible, such that a user can compress the first bulb 102 to displace the air within the first bulb 102 into the stem 106 and second bulb 104.

Air (or another fluid, typically a gas) traveling from the first bulb 102 and into the second bulb 104 can displace the liquid and/or air that is already disposed in the second bulb 104. Displacing the liquid and/or air can result in the liquid being propelled out of an opening defined by the second bulb. The liquid that is propelled out of the opening can end up within the patient's ear to effectively deliver the liquid to the desired location within the patient's ear/ear canal/middle ear.

In an embodiment, the device 100 can be configured to dispense an amount of fluid that ranges from 0.05 ml to 0.5 ml from the second bulb. In an embodiment, the device 100 can be configured to dispense an amount of fluid that ranges from 0.05 ml to 1 ml. In an embodiment, the device 100 can be configured to dispense an amount of fluid that ranges from 0.05 ml to 5 ml. In an embodiment, the device 100 can be configured to dispense an amount of fluid that ranges from 0.1 ml to 0.5 ml. In an embodiment, the device 100 can be configured to dispense an amount of fluid that ranges from 0.1 ml to 1 ml. In an embodiment, the device 100 can be configured to dispense an amount of fluid that ranges from 0.1 ml to 5 ml.

In various embodiments, the first bulb 102 is coupled to the stem 106, and the stem 106 is coupled to the second bulb 104. The first bulb 102 can be coupled to a first end of the stem 106 and the second bulb 104 can be coupled to a second end of the stem 106. The first end can be on the opposite end of the stem 106 from the second end.

The device 100 can be configured to dispense or discharge fluid (liquid or gas) from the second bulb 104 through an opening. The second bulb 104 can define an opening, such as to allow fluid (liquid or gas) to enter or exit the device 100, specifically enter or exit the second bulb 104. FIGS. 17-22 show various embodiments of the opening defined by the second bulb 104. The opening defined by the second bulb 104 can be located opposite from the connection between the stem 106 and the second bulb 104, such as the distal end of the second bulb 104. The end of the second bulb 104 that defines the opening can be blunt or rounded, such that it is not considered sharp. The second bulb 104 can be blunt or rounded, such as to prevent injuring a patient's ear while dispensing liquid from the device into the patient's ear/ear canal/ear drum.

In various embodiments, the device 100 can include a polymer, such as a transparent or translucent polymer (such as polyethylene, polypropylene, and combinations thereof), and can be made using injection or blow molding techniques (for example). Rubber is also a suitable material for some implementations. A transparent or translucent polymer can allow a person to see into the inner portions of the device 100, such as to determine if there is liquid in the second bulb 104 or how much liquid is in the second bulb 104. In various embodiments, the device 100 can include polystyrene or polyethylene. In some embodiments, the device 100 can be monolithic, such that the first bulb 102, the second bulb 104 and the stem 106 are formed or created together or from a single piece of polymer. The device 100 can be monolithic, such that the device 100 is a single continuous piece of polymer. In various embodiments, the device 100 can be configured such that no part of the device can fall off, separate or become lodged within the patient's ear/ear canal.

Figure 2:
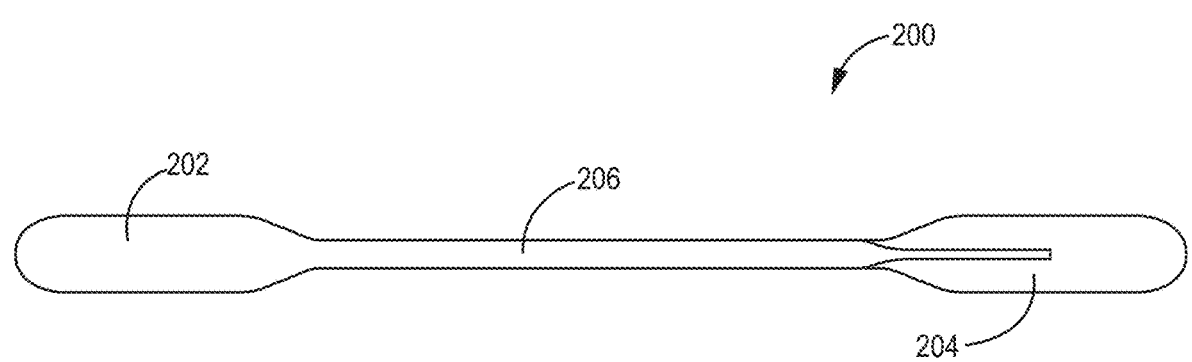
FIG. 2 is a front view of a device for dispensing medication, according to an embodiment.

FIG. 2 shows a front view of a device 200, according to an embodiment. The device 200 can include a first bulb 202, a second bulb 204 and a stem 206. The stem prevents drops from entering the first bulb 202 and wasting medicine, which would increase costs. In various embodiments, the stem 206 can terminate within the second bulb 204, such that a portion of the stem 206 is within the second bulb 204. The stem 206 can extend past the wall defining the second bulb 204 and into the inner cavity defined by the second bulb 204. In an embodiment, less than 10% of the stem 206 is within the second bulb 204. In an embodiment, less than 25% of the stem 206 is within the second bulb 204. In an embodiment, less than 50% of the stem 206 is within the second bulb 204. In an embodiment, at least 5% of the stem 206 is within the second bulb 204. In an embodiment, at least 10% of the stem 206 is within the second bulb 204. In an embodiment, at least 25% of the stem 206 is within the second bulb 204. In an embodiment, at least 50% of the stem 206 is within the second bulb 204.

In various embodiments, the first end of the stem 206 is coupled to or extends from the first bulb 202 and the second end of the stem 206 is coupled to, extends from, or within the second bulb 204. In an embodiment, the second end of the stem 206 can be tapered, such that that a cross-section near the end of the stem 206 is smaller than a cross-section taken farther away from the end of the stem 206. It is possible to combine the various components discussed herein.

Figure 3:
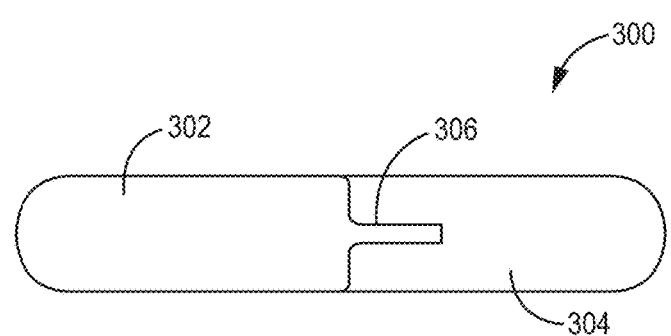
FIG. 3 is a front view of a device for dispensing medication, according to an embodiment.

FIG. 3 shows a front view of a device 300, according to an embodiment. The device 300 can include a first bulb 302, a second bulb 304 and a stem 206. In an embodiment, the stem 306 can be enclosed within the first bulb 302 and the second bulb 304, such that the entire stem 306 is within the device 300 and the stem 306 is not exposed to the environment. In such an embodiment, the outer most portion of the device 300 can have a consistent size along a portion of the device. The outer most portion of the device 300 can have a consistent size along the length of the device, such that a cross-section take a first point has the same outer size and shape as a cross-section take at a second point.

In an embodiment, at least 25% of the length of the device 300 has a consistent outer size and shape. In an embodiment, at least 50% of the length of the device 300 has a consistent outer size and shape. In an embodiment, at least 75% of the length of the device 300 has a consistent outer size and shape. In an embodiment, at least 90% of the length of the device 300 has a consistent outer size and shape. Element 304 can be modified to include any combination of the implementations and components described herein.

Figure 4:
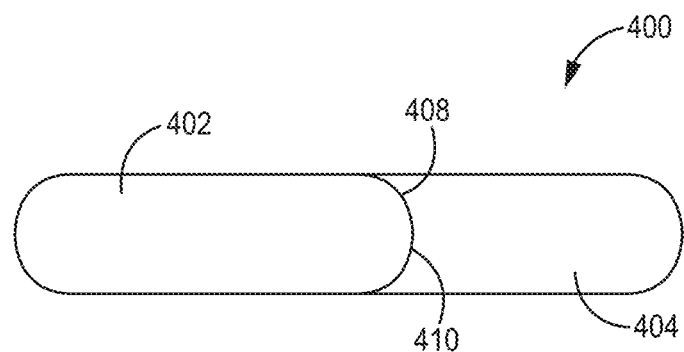
FIG. 4 is a front view of a device for dispensing medication, according to an embodiment.

FIG. 4 shows a front view of a device 400, according to an embodiment. In an embodiment, the device 400 can include a first bulb 402, a second bulb 404 and a separator element 408. The separator element 408 can be disposed within the device 400 to define between the first bulb 402 and the second bulb 404. The first bulb 402 can be compressible. The first bulb 402 can be configured to hold air. The second bulb 404 can be configured to hold air and/or liquid. The separator element 408 can prevent liquid in the second bulb 404 from entering the first bulb 402. Element 404 can be modified to include any combination of the implementations and components described herein.

The separator element 408 can define a passage 410. The passage 410 can be an opening or aperture in the separator element 408 to allow air from the first bulb 402 to transfer into the second bulb 404 in order to displace the liquid in the second bulb 404 and force the liquid out of an opening defined by the second bulb 404. In an embodiment, the separator element 408 can be arced, such as shown in FIG. 4. In an embodiment, the separator element 408 can include a hollow stem or shaft, similar to the device 300 shown in FIG. 3. At least a portion of the stem or shaft can be tapered.

The device 400 can have a consistent cross-section over at least 75% of the length of the device 400. In an embodiment, the device 400 can have a circular cross-section. In an embodiment, the device 400 can have a circular cross-section over at least 75% of the length of the device 400.

Figure 5:
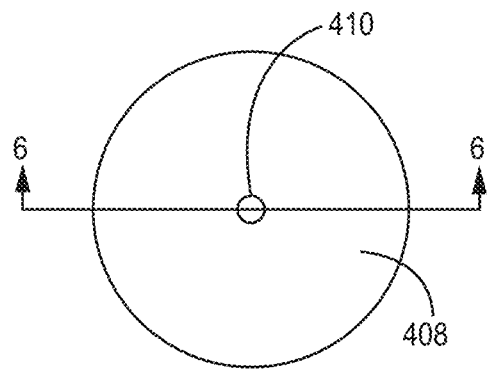
FIG. 5 is a top view of a separating element, according to an embodiment.
Figure 6:
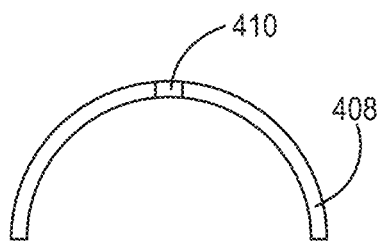
FIG. 6 is a cross-section view of a separating element, according to an embodiment.

FIG. 5 shows a top view of the separating element 408. FIG. 6 shows a cross-section of the separating element 408 taken along line 6-6 in FIG. 5. The separating element 408 can be circular, similar to the cross-section of the device 400. The separating element can define a passage 410. In an embodiment, the passage 410 can be circular. The passage 410 can be small such that liquid in the second bulb 404 does not pass through the passage 410 and into the first bulb 402. The separating element 408 can be domed, curved, or arced. In an embodiment, the separating element 408 can include polymer, rubber, or a combination thereof.

Figure 7:
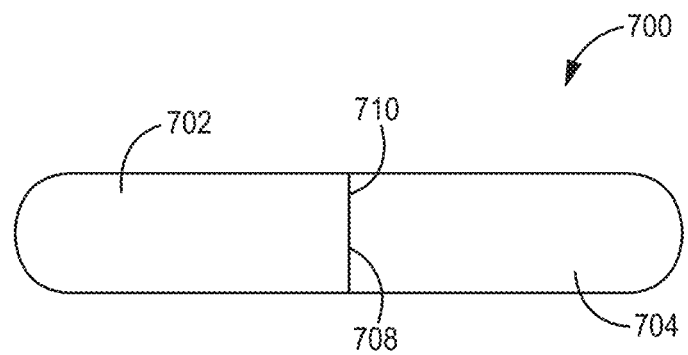
FIG. 7 is a front view of a device for dispensing medication, according to an embodiment.

FIG. 7 shows a front view of a device 700, according to an embodiment. In an embodiment, the device 700 can include a first bulb 702, a second bulb 704 and a separator element 708. The separator element 708 can be disposed within the device 700 to define between the first bulb 702 and the second bulb 404. The first bulb 702 can be compressible. The first bulb 702 can be configured to hold air. The second bulb 704 can be configured to hold air and/or liquid. The separator element 708 can prevent liquid in the second bulb 704 from entering the first bulb 702. The separator element 708 can be flat or planar, or have a different configuration.

Figure 8:
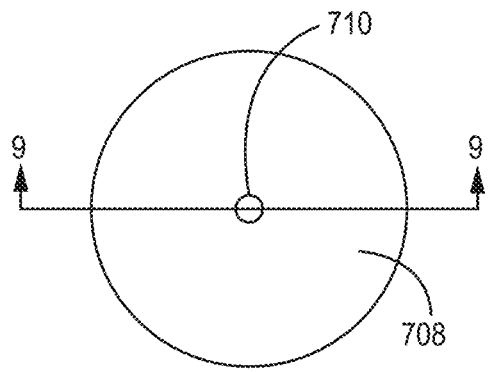
FIG. 8 is a top view of a separating element, according to an embodiment.
Figure 9:
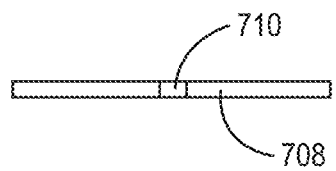
FIG. 9 is a cross-section view of a separating element, according to an embodiment.

FIG. 8 shows a top view of the separating element 708. FIG. 9 shows a cross-section of the separating element 708 taken along line 9-9 in FIG. 8. The separating element 708 can define a passage 710. The passage 710 can be circular. The passage 710 can be sufficiently small to prevent liquid in the second bulb 704 from passing into the first bulb 702.

Figure 10:
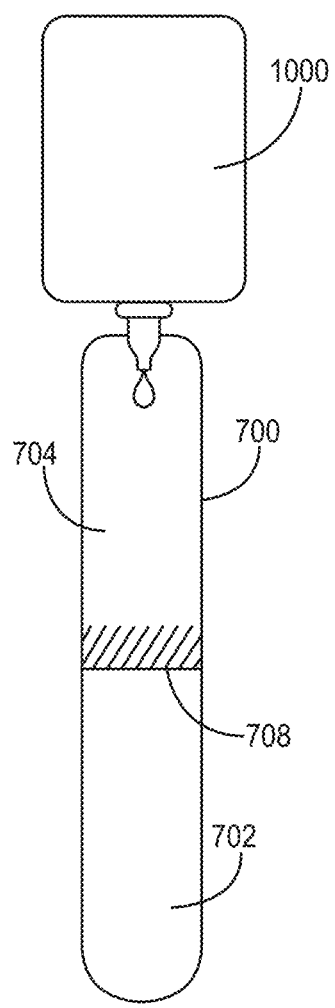
FIG. 10 is a front view of a device being filled with a liquid, according to an embodiment.

FIG. 10 shows a front view of a device 700 being filled with a liquid, according to an embodiment. In various embodiments, the first bulb 702 can be configured to be filled with air and the second bulb 704 can be configured to be at least partially filled with a liquid. Element 1000 represents multiple possible ear dropper bulbs with varying dropper tip sizes and designs.

In various embodiments, liquid can be dispensed into the second bulb 704 through the opening defined by the second bulb 704. In some scenarios, a user can insert a portion of a bottle 1000 through the opening and into the second bulb 704. At least some of the liquid can be dispensed into the second bulb 704. The bottle 1000 can be representative of bottles commercially available for storing and dispensing medications for a patient's ear, commonly referred to as ear drops. As such, the opening (as shown in FIGS. 17-22) defined by the second bulb 704 can be configured to accommodate bottles and bottle tips of various shapes and sizes, such that a single embodiment of the device can be filled by different sized or shaped bottles. The separator element 708 can prevent liquid from entering the first bulb 702 from the second bulb 704.

Figure 11:
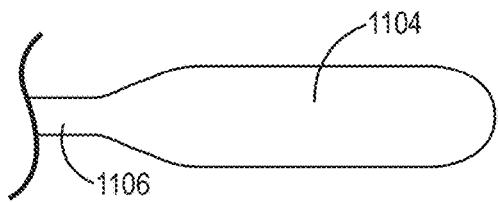
FIG. 11 is a front view of a second bulb, according to an embodiment.

The second bulb can have various different shapes, such as oval, conical, or tapered. Various embodiments of the second bulb are shown in FIGS. 11-16. The second bulb can be shaped to protect a patient's ear from blunt trauma and maintains an air-tight seal. FIG. 11 shows a front view of a second bulb 1104, according to an embodiment. The second bulb 1104 can include a rounded surface that defines the opening. The end of the second bulb 1104 that is not coupled to the stem 1106 can be rounded. The second bulb 1104 can have a circular cross-section.

Figure 12:
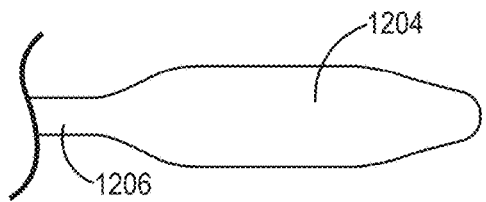
FIG. 12 is a front view of a second bulb, according to an embodiment.

FIG. 12 shows a front view of a second bulb 1204, according to an embodiment. The second bulb 1204 can be tapered towards the end that defines the opening. The second bulb 1204 can be tapered with a rounded or blunt end.

Figure 13:
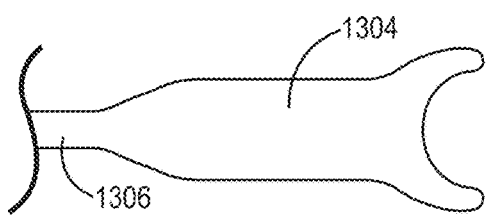
FIG. 13 is a front view of a second bulb, according to an embodiment.

FIG. 13 shows a front view of a second bulb 1304, according to an embodiment. The end of the second bulb 1304 that defines the opening can be recessed. The recessed end can be rounded. In an embodiment, the rounded portion can define half of a sphere. In various embodiments, the opening can be the most recessed portion of the end of the second bulb 1304.

Figure 14:
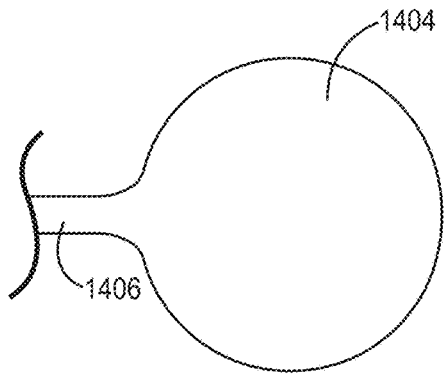
FIG. 14 is a front view of a second bulb, according to an embodiment.

FIG. 14 shows a front view of a second bulb 1404, according to an embodiment. In an embodiment, the second bulb 1404 can be spherical, such that the second bulb 1404 generally defines a sphere with the exception of the connection between the second bulb 1404 and the stem 1406, and in some embodiments, with the exception of the portion of the second bulb 1404 that defines the opening.

Figure 15:
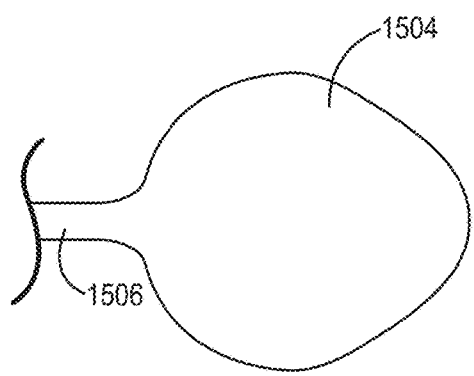
FIG. 15 is a front view of a second bulb, according to an embodiment.

FIG. 15 shows a front view of a second bulb 1504, according to an embodiment. The second bulb 1504 can have a mushroom shape. The second bulb 1504 can be tapered towards both ends. In an embodiment, the end that defines the opening is tapered more than the end that is connected to the stem 1506, such that the portion of the bulb 1504 that is tapered towards the stem 1506 is shorter than the portion of the bulb 1504 that is tapered towards the opening.

Figure 16:
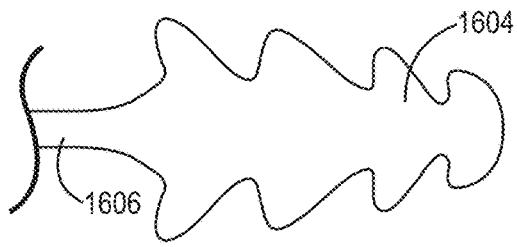
FIG. 16 is a front view of a second bulb, according to an embodiment.

FIG. 16 shows a front view of a second bulb 1604, according to an embodiment. In an embodiment, the second bulb 1604 can be tapered with one or more ridges along the length. The second bulb 1604 can include rounded ridges, such as shown in FIG. 16, and can include alternatively a half-sphere shape.

Figure 17:
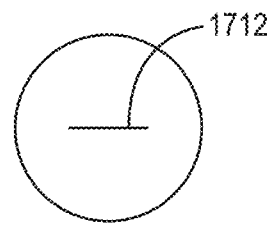
FIG. 17 is an end view of a device, according to an embodiment.

FIGS. 17-22 show various embodiments of the opening defined by the second bulb. FIG. 17 shows an end view of a device, according to an embodiment. The second end can define an opening 1712. The opening 1712 can be a slit. The second bulb can be flexible such that the slit can be opened, such as when dispensing into or out of the second bulb. In various embodiments, in a resting state, the opening 1712 can be closed, such that the two edges of the second bulb that define the slit can abut against each other.

In various embodiments, an opening can be configured to provide a seal, such as to substantially prevent any liquid from exiting the second bulb unintentionally. For example, an opening can provide a seal, such that if the device is turned vertically with the second bulb pointed down the liquid will remain within the second bulb designed to prevent trauma to the ear or ear canal, and designed to create an adequate seal for propulsion of drops.

Figure 18:
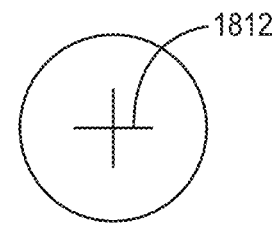
FIG. 18 is an end view of a device, according to an embodiment.

FIG. 18 shows an end view of a device, according to an embodiment. In an embodiment, the opening 1812 can include two slits. The slits can be perpendicular with each other. In an embodiment, the two slits are the same length and intersect at the middle of each slit.

Figure 19:
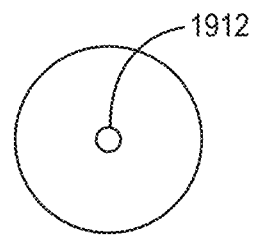
FIG. 19 is an end view of a device, according to an embodiment.

FIG. 19 shows an end view of a device, according to an embodiment. In an embodiment, the opening 1912 can be circular. The opening 1912 can be open, such that it defines an aperture.

Figure 20:
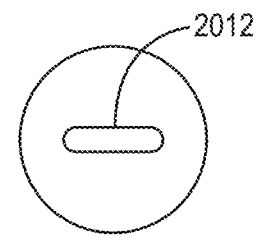
FIG. 20 is an end view of a device, according to an embodiment.

FIG. 20 shows an end view of a device, according to an embodiment. In an embodiment, the opening 2012 can be oval shaped. In other embodiments, the opening can be rectangular or rectangular with rounded corners.

Figure 21:
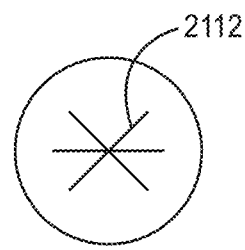
FIG. 21 is an end view of a device, according to an embodiment.

FIG. 21 shows an end view of a device, according to an embodiment. In an embodiment, the opening 2112 can include three or more slits. In an embodiment, the slits can intersect at the midpoint of each slit.

Figure 22:
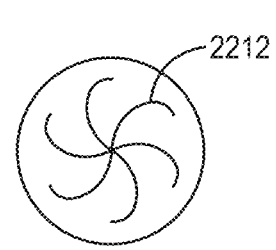
FIG. 22 is an end view of a device, according to an embodiment.

FIG. 22 shows an end view of a device, according to an embodiment. In an embodiment, the opening 2212 can include a curved slit. In an embodiment, the opening 2212 can include a plurality of curved slits. The slits can intersect at the midpoint of each slit.

Figure 23:
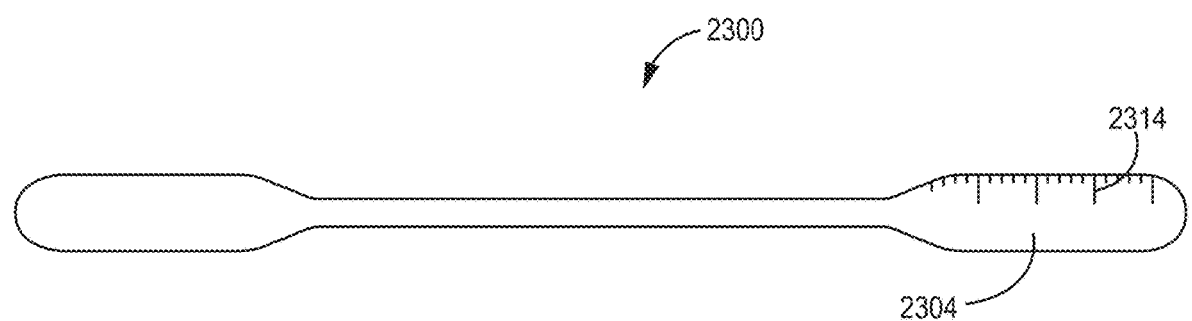
FIG. 23 is a front view of a device, according to an embodiment.

FIG. 23 is a front view of a device 2300, according to an embodiment. In various embodiments, the device 2300 can include volumetric indicia 2314, such as indicia that show the user how much liquid is in the second bulb 2304. In an embodiment, the device 2300 can be positioned vertically for the liquid level to align with the volumetric indicia 2314. In an embodiment, the volumetric indicia 2314 can be in increments of 1 ml or less, 0.5 ml or less, 0.1 ml or less, 0.05 ml or less, or 0.01 ml or less. In an embodiment, the volumetric indicia 2314 can be in increments of a single drop, such that a user can determine how many drops he/she has dispensed into the second bulb 2304.

Figure 24:
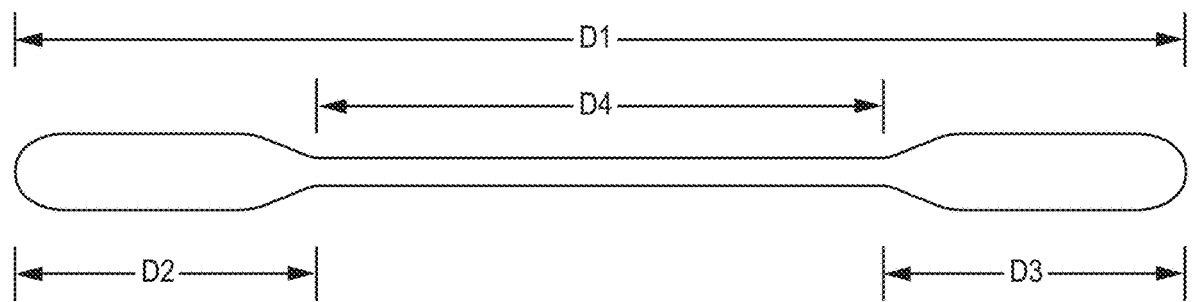
FIG. 24 is a front view of a device, according to an embodiment.

FIG. 24 is a front view of a device, according to an embodiment. The device can have an overall length, D1, of at least 0.5 cm and not more than 15 cm. In an embodiment, the device can have an overall length of at least 1 cm and not more than 10 cm. In an embodiment, the device can have an overall length of at least 1 cm and not more than 5 cm. In an embodiment, the device can have an overall length of at least 1 cm and not more than 3 cm.

In an embodiment, the length of the first bulb D2 can be substantially equal to the length of the second bulb D3. In an embodiment, the length of the stem D4 can be larger than the length of the first bulb or the length of the second bulb. In an embodiment, the stem can have a length of at least 0.5 cm and not more than 10 cm. In an embodiment, the stem can have a length of at least 1 cm and not more than 3 cm.

In an embodiment, the first bulb can have substantially the same volume as the second bulb. In an embodiment, the first bulb can have a larger volume than the second bulb. In an embodiment, the second bulb can have a larger volume than the first bulb. In an embodiment, the volume of the first bulb or second bulb can be at least 1 ml and not more than 50 ml. In an embodiment, the volume of the first bulb or second bulb can be at least 1 ml and not more than 25 ml. In an embodiment, the volume of the first bulb or second bulb can be at least 1 ml and not more than 10 ml. In an embodiment, the volume of the first bulb or second bulb can be at least 1 ml and not more than 5 ml. In an embodiment, the volume of the first bulb or second bulb can be at least 1 ml and not more than 3 ml. In an embodiment, the volume of the first bulb or second bulb can be at least 0.5 ml and not more than 2 ml.

Figure 25:
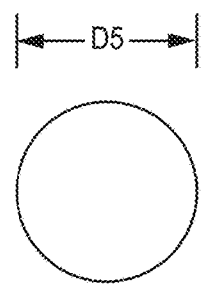
FIG. 25 is an end view of a device, according to an embodiment.

FIG. 25 is an end view of a device, according to an embodiment. In various embodiments, the first bulb and the second bulb can have the same diameter. In an embodiment, the first bulb or the second bulb can have a diameter of at least 1 mm and not more than 30 mm. In an embodiment, the first bulb or the second bulb can have a diameter of at least 2 mm and not more than 20 mm. In an embodiment, the first bulb or the second bulb can have a diameter of at least 5 mm and not more than 10 mm.

FIGS. 26-30 show various steps in a method for delivering a liquid to the patient's ear. FIG. 26 is a front view of a device 2600. The device 2600 is shown empty in FIG. 26.

FIG. 27 shows the device 2600 being at least partially filled with a liquid. The method can include dispensing the liquid into the second hollow bulb of a device by inserting a tip of a bottle of liquid into an opening defined by the second hollow bulb. Once the tip of the bottle of liquid is inserted into the opening, the liquid can be dispensed into the second bulb of the device 2600.

After the liquid is dispensed into the device 2600, the tip of the bottle can be removed from the opening. FIG. 27 shows the device 2600 after the liquid has been dispensed into the device 2600 and the bottle of liquid has been removed.

The device 2600 can be aligned with the patient's ear. Specifically, the second bulb can be inserted into the ear canal, such as shown in FIG. 29. Once the device 2600 is aligned with the patient's ear or ear canal, an air tight seal can be achieved, the user can compress the first bulb to project or propel the liquid from the second bulb into the patient's ear or ear canal or middle ear as shown in FIG. 30.

Figure 31:
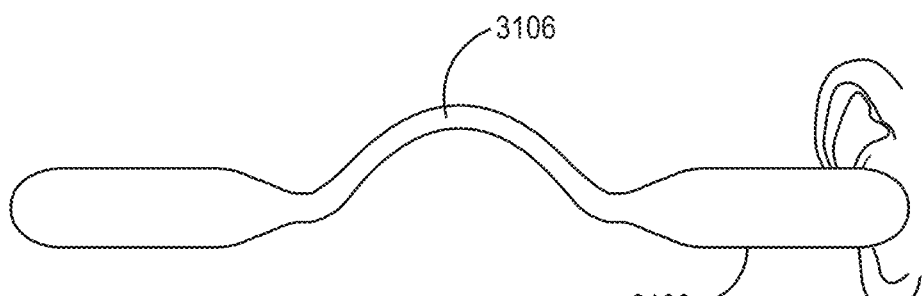
FIG. 31 is a front view of a device aligned with a patient's ear, according to an embodiment.

FIG. 31 shows a front view of a device 3100 aligned with a patient's ear, according to an embodiment. In various embodiments, the device 3100 can include a stem 3106. The stem 3106 can be flexible, such that if a user applies too much pressure against the patient's ear, the stem 3106 can flex or deform, such as to absorb at least a portion of the force. In an embodiment, the stem 3106 can be configured to flex or deform under forces large enough to cause blunt trauma to the patient. The stem 3106 can absorb a portion of the force in order to decrease the chances of damaging the patient's ear/ear canal.

Figure 32:
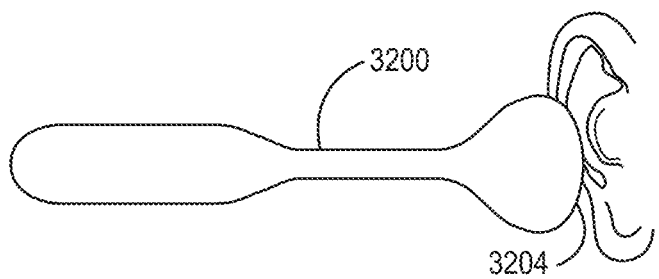
FIG. 32 is a front view of a device aligned with a patient's ear, according to an embodiment.
Figure 33:
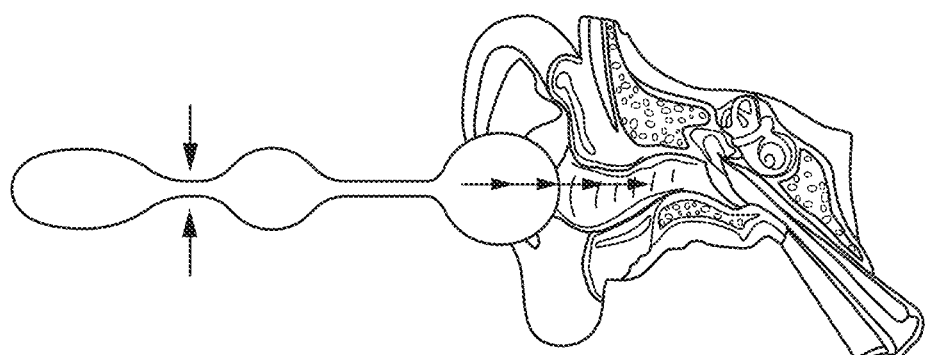
FIG. 33 is a front view of a device aligned with a patient's ear, according to an embodiment.

FIG. 32 shows a front view of a device 3200 aligned with a patient's ear/ear canal/middle ear, according to an embodiment. In various embodiments, the device 3200 can include a second bulb 3204. The second bulb 3204 can be flexible, such that if a user applies too much pressure against the patient's ear, the second bulb 3204 can flex or compress, such as to absorb at least a portion of the force. The second bulb 3204 can absorb a portion of the force in order to decrease the chances of damaging the patient's ear. It will be understood that the devices of the present application can be constructed so as to have the ability to propel fluid into the ear canal or middle ear. FIG. 33 shows the device of FIG. 33.

Figure 34:
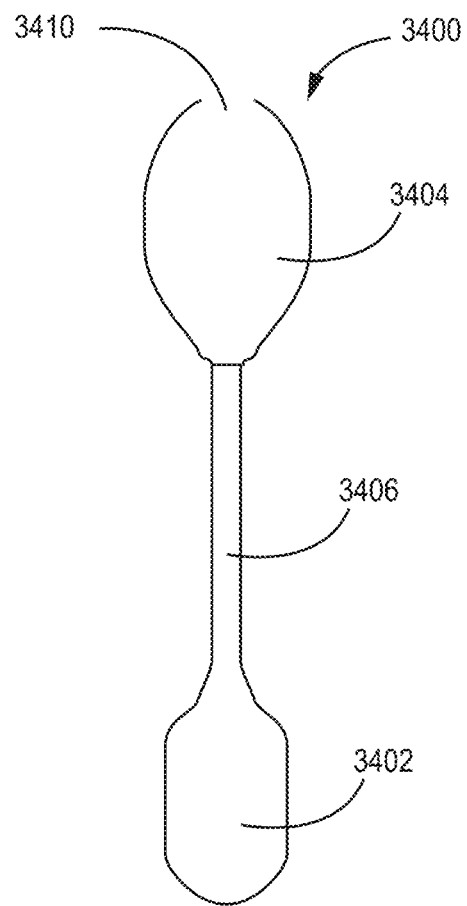
FIG. 34 is a front view of a device for dispensing medication, according to an embodiment.
Figure 35:
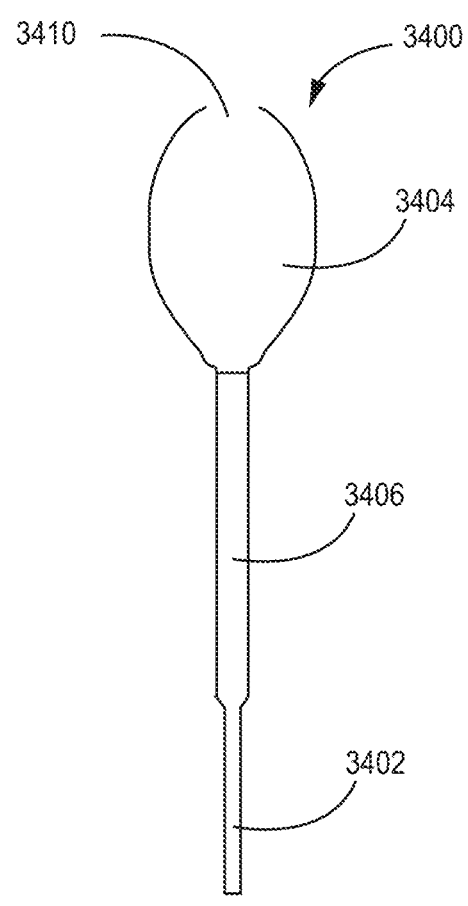
FIG. 35 is a side view of a device for dispensing medication, according to an embodiment.
Figure 38:
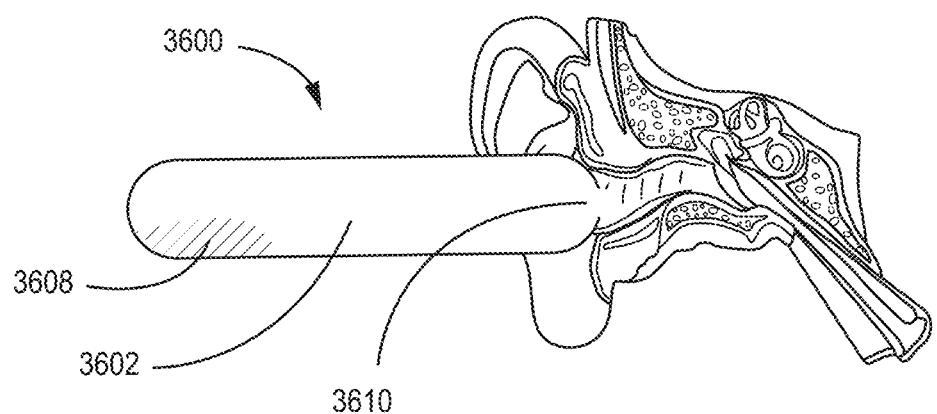
FIG. 38 is a front view of a device aligned with a patient's ear, according to an embodiment.
Figure 39:
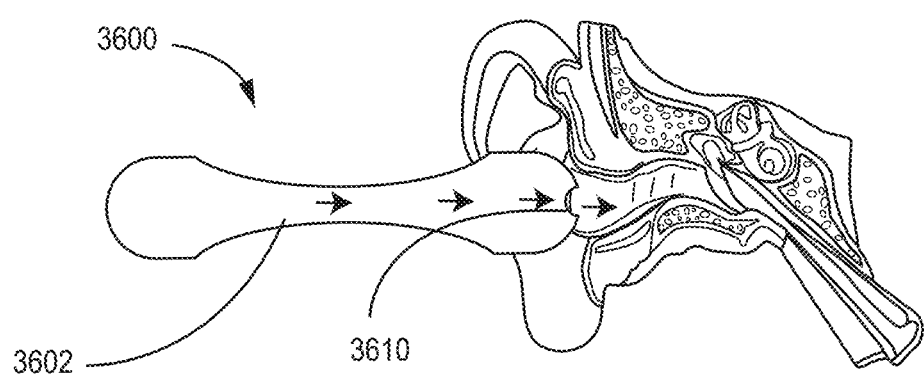
FIG. 39 is a front view of a device aligned with a patient's ear, according to an embodiment.

FIGS. 34 and 35 show a device 3400 having a reservoir 3404, a flat handle 3402, and a stem 3406 connecting the reservoir 3404 and the handle 3402. In FIG. 34 the handle 3402 is shown in front view, while in FIG. 35 the handle 3402 is shown in side view. Typically the stem 3406 is solid, as opposed to being hollow, in the embodiment shown. The stem can be, for example, round or flat. If flat, it can be as wide, for example, as the width of the reservoir 3404. During use a bottle of medication is positioned at opening 3410 at the top of the device 3400, and one or more drops of medication is dripped or sprayed (or otherwise added) to the reservoir 3404. This medication collects at the bottom of the reservoir 3404 and can then be poured or squeezed into a patient's ear (see FIGS. 38 and 39, showing a modified version of device 3400 without stem or handle but similar mode of operation). With this design, delivery of the medication is typically by pouring rather than squeezing. In an embodiment, the device 3400 can be configured to dispense an amount of fluid that ranges from 0.05 ml to 0.5 ml. In an embodiment, the device can be configured to dispense an amount of fluid that ranges from 0.05 ml to 1 ml. In an embodiment, the device 3400 can be configured to dispense an amount of fluid that ranges from 0.05 ml to 5 ml.

Figure 36:
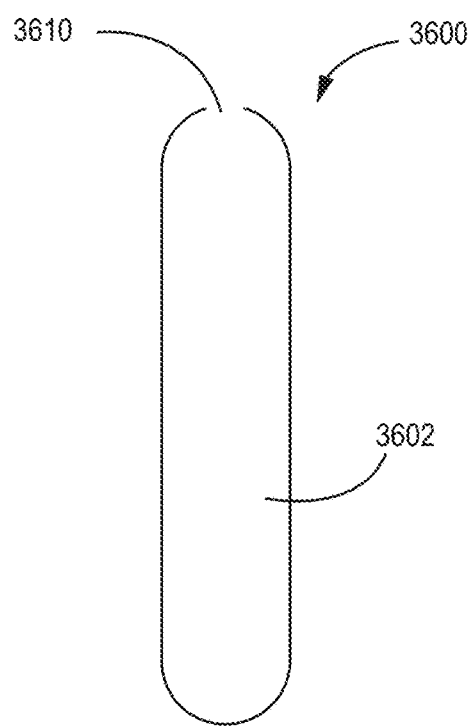
FIG. 36 is a front view of a device for dispensing medication, according to an embodiment.
Figure 37:
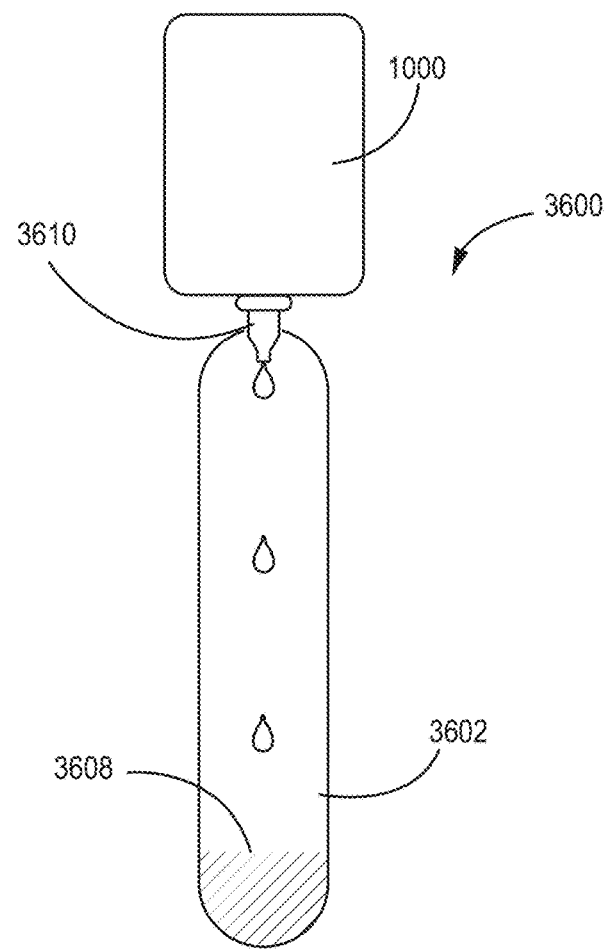
FIG. 37 is a front view of a device for dispensing medication, according to an embodiment, showing the device with medication being added.

FIGS. 36 and 37 show a stemless design wherein device 3600 includes a single reservoir 3602, typically elongate, with an opening 3610. Bottle 1000 is representative of bottles commercially available for storing and dispensing medications for a patient's ear, and is used to deliver medication 3608 into the reservoir 3602. FIGS. 38 and 39 show the stemless design of device 3600, which is placed in the outer ear and squeezed to deliver the medication into the inner ear. Alternatively the medication can be delivered by tipping the ear into a more upward orientation, with the device 3600 rotated so that opening 3610 is pointing downward so that the medication 3608 collects near the opening 3610 and either flows by gravity into the ear, or is assisted by squeezing of the reservoir 3602 to provide pressure and air flow to direct the medication into the ear.

Figure 40:
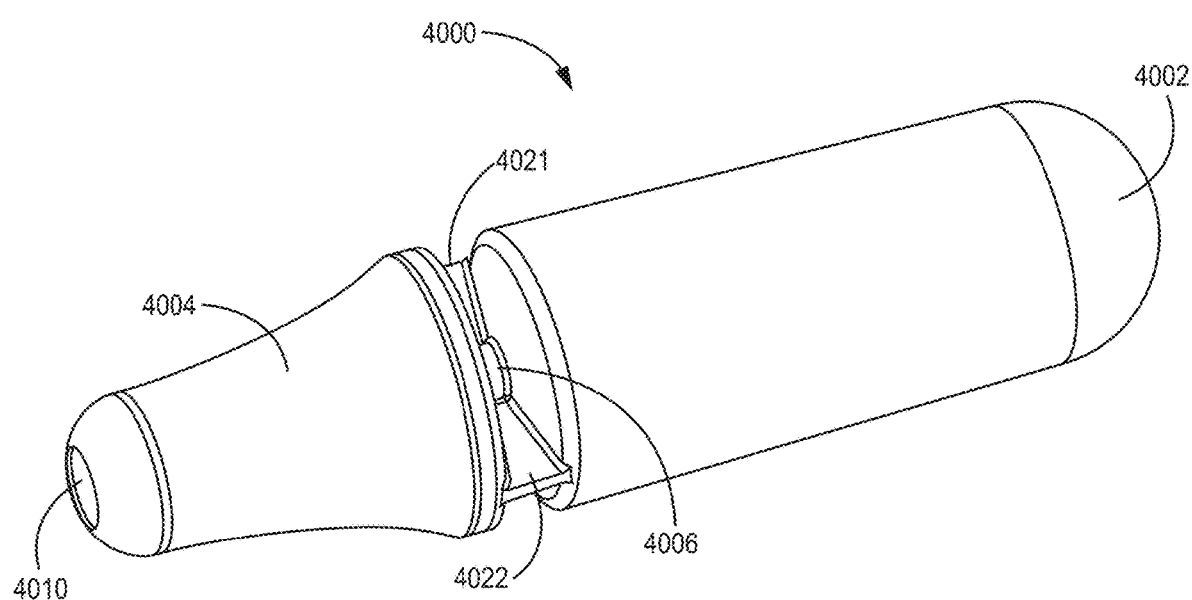
FIG. 40 is a perspective view of a device for dispensing medication, according to an embodiment.

FIG. 40 is a perspective view of a device 4000 for dispensing medication, according to an alternative embodiment. The device has a first hollow bulb 4002 and a second hollow bulb 4004 connected by a hollow stem 4006. The second hollow bulb has an opening 4010 at one end to allow fluid flow out of the bulb 4004. Both the bulb 4002 and bulb 4004 have openings connected to hollow stem 4006 such that the first bulb 4002 and second bulb 4004 are in fluid communication via stem 4006. Fluids such as air or liquid can pass from one bulb to the other bulb through stem 4006.

The second bulb 4004 is configured to receive a liquid medication. For example, the liquid can be dispensed into the hollow bulb 4004 via a bottle of liquid, similar to the method shown and described in connection with FIGS. 26 and 27. Other methods of dispensing liquid into the bulb 4004 are contemplated, such as insertion of liquid into the hollow bulb 4004 using a syringe.

The bulb 4002 is filled with fluid. In one embodiment, the bulb 4002 is filled mostly with a volume of air. The bulb 4002 may alternatively be filled with both air and liquid, or only with a volume of liquid. The bulb 4004 is filled with fluid. In one embodiment, the bulb 4004 is filled mostly with a volume of liquid. The bulb 4004 may alternatively be filled with both air and liquid, or only with a volume of air.

In one embodiment, it is desirable to prevent liquid from entering the bulb 4002. In this case, the internal diameter of the hollow stem 4006 may be narrowed. In an embodiment, the internal diameter of the hollow stem 4006 may be smaller than about 0.10 inches. The stem 4006 may alternatively be smaller than about 0.060 inches. The stem 4006 may alternatively be smaller than about 0.040 inches. The stem 4006 may alternatively be smaller than about 0.020 inches. If the diameter of the hollow stem 4006 cannot be sufficiently narrowed during the manufacturing process, an insert may be put into or near the opening of the hollow stem 4006. The insert may be an O-ring or a plug. In an embodiment, the insert may narrow the internal diameter of the hollow stem 4006 to be smaller than about 0.10 inches. Alternatively, the insert may narrow the internal diameter of the hollow stem 4006 to be smaller than about 0.060 inches. Alternatively, the insert may narrow the internal diameter of the hollow stem 4006 to be smaller than about 0.040 inches. Alternatively, the insert may narrow the internal diameter of the hollow stem 4006 to be smaller than about 0.020 inches. The insert may be placed into the hollow stem 4006 during manufacture of the device 4000, or may be placed after manufacture. The insert may be fused to the hollow stem 4006. The small diameter of the insert will limit the amount of fluid flow from bulb 4004 into bulb 4002.

Alternatively, a valve could be inserted into or near the hollow stem 4006. The valve prevents fluid in bulb 4004 from passing through the hollow stem 4006 into the bulb 4002, while allowing fluid to flow from the bulb 4002 into the bulb 4004. The valve may be a flap, a one-way valve, a check-valve, or another type of suitable valve. In an embodiment, pressure applied to the bulb, such as by squeezing the bulb 4002 with the fingers, actuates the valve, allowing fluid, such as air, to pass from bulb 4002 through the hollow stem 4006 and into the bulb 4004, while preventing fluid in bulb 4004 from passing through hollow stem 4006 and into the bulb 4002.

The first bulb 4002 is configured to be compressible. For example, the bulb 4002 can be compressed between a user's two fingers. Compressing the bulb 4002 puts pressure on the fluid inside of the bulb, which causes the fluid to exit the bulb 4002 through the hollow stem 4006 and flow into the second hollow bulb 4004. The pressure may then cause fluid in the second bulb 4004 to exit the opening 4010, allowing liquid medication to be propelled into a patient's ear canal in a similar manner to that shown and described in relation to FIG. 33.

The device 4000 may also comprise support members 4021, 4022. The support members 4021, 4022 may be disposed on each side of the hollow stem 4006. The support members 4021, 4022 span the gap between bulb 4002 and bulb 4004, connecting the two bulbs and providing stability. In one embodiment the support members 4021, 4022 are flat and define a plane that intersects the stem 4006. In alternative embodiments, the support members 4021, 4022 could be disposed such that they do not define a plane. It is contemplated that in alternative embodiments there could be more than two support members. In some embodiments, device 4000 can be monolithic, such that the first bulb 4002, the second bulb 4004, the stem 4006, and the support members 4021, 4022 are formed or created together or from a single piece of polymer. The device 4000 can be monolithic, such that the device 4000 is a single continuous piece of polymer. In various embodiments, the device 4000 can be configured such that no part of the device can fall off, separate, or become lodged within the patient's ear canal.

In various embodiments, the device 4000 can be made from a polymer, such as a transparent or translucent polymer (such as polyethylene, polypropylene, and combinations thereof), and can, for example, be made using injection or blow molding techniques. Rubber is also a suitable material for some implementations. A transparent or translucent polymer can allow a person to see into the inner portions of the device 4000, such as to determine if there is liquid in the second bulb 4004 or how much liquid is in the second bulb 4004. In various embodiments, the device 4000 can include polystyrene or polyethylene.

Figure 41:
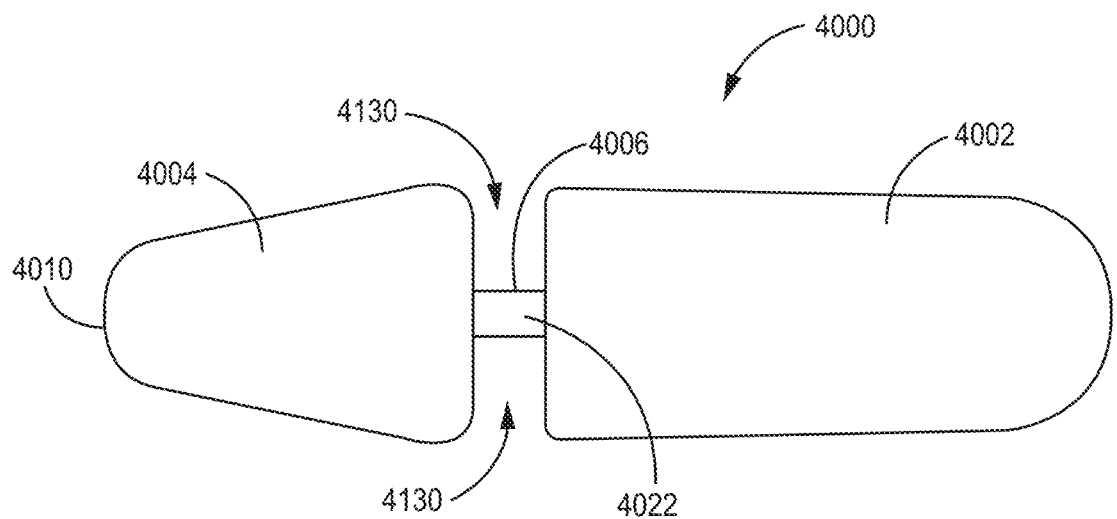
FIG. 41 is a side view of the device of FIG. 40.

FIG. 41 is a side view of the device 4000. FIG. 41 shows that the first bulb 4002 and the second bulb 4004 are separated by a gap 4130, but connected by the stem 4006. FIG. 41 also shows the outside edge of support member 4022. The support members 4021, 4022 form a plane, and therefore only one edge of the support member 4022 can be seen from the side view perspective.

Figure 42:
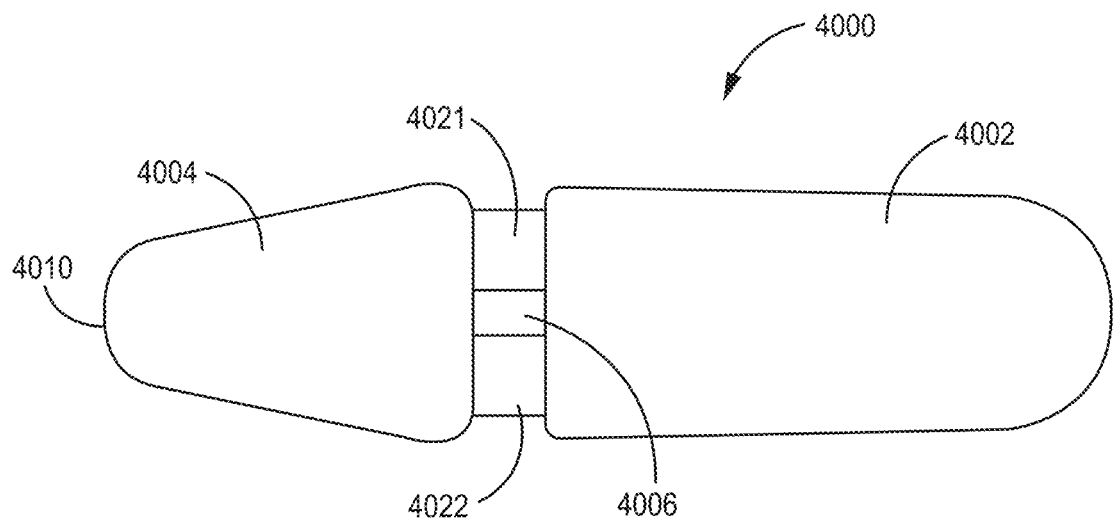
FIG. 42 is a top view of the device of FIG. 40.

FIG. 42 is a top view of the device 4000. The support members 4021, 4022 are seen on both sides of the hollow stem 4006. The support members 4021, 4022 span the gap between first bulb 4002 and second bulb 4004. In the embodiment shown in FIG. 42, the support members 4021, 4022 and the stem 4006 are in contact with the stem 4006. In alternative embodiments, the support members 4021, 4022 could be configured so that the support members 4021, 4022 are not in contact with the stem 4006 (e.g., there could be a gap between the support members 4021, 4022 and the stem 4006).

In an embodiment, the stem 4006 and support members 4021, 4022 flexibly couples the first bulb 4002 and second bulb 4004. As can be seen in FIG. 42, the support members 4021, 4022 provide stability to prevent the stem 4006 from moving in the side-to-side direction. However, as can be seen in FIG. 41, the support members 4021, 4022 do not provide stability in the up/down direction. This can be seen more clearly in FIG. 43.

Figure 43:
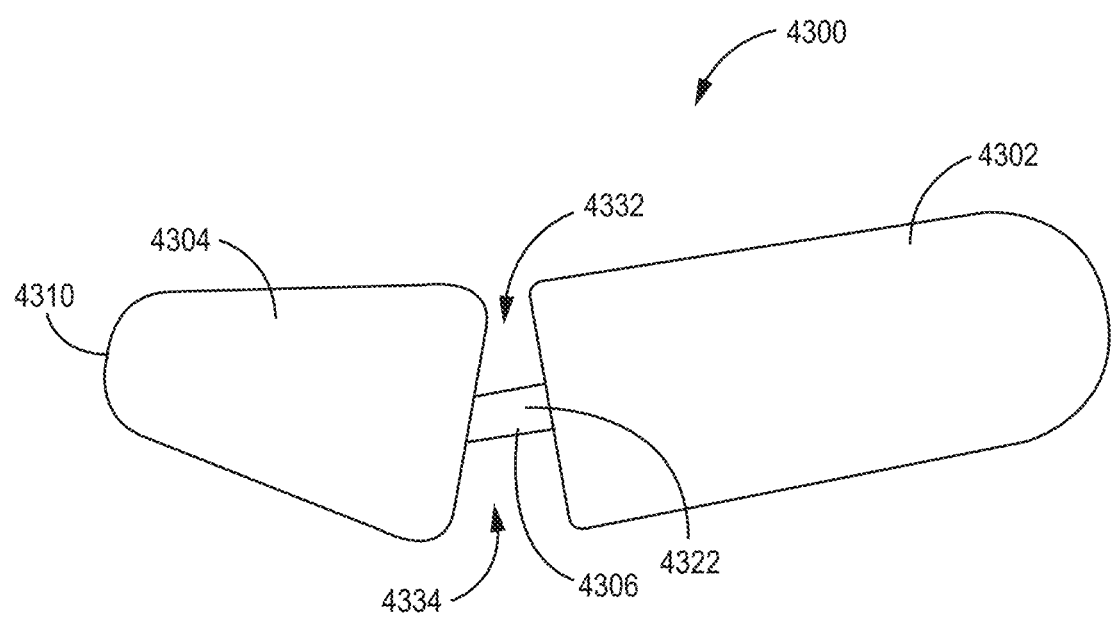
FIG. 43 is perspective view of a device for dispensing medication, according to an embodiment.

FIG. 43 is side view of a device 4300 with a stem 4306 that flexibly couples a first hollow bulb 4302 and a second hollow bulb 4304. The device 4300 can be similar to the device 4000, shown and described in connection with FIGS. 40-42. The device 4300 can have support members. FIG. 43 shows a support member 4322 in profile. The support member 4322 is similar to the support member 4022 in FIGS. 40-42. The support members 4322 and the stem 4306 of device 4300 is formed of a material that is sufficiently flexible to allow the first bulb 4302 and second bulb 4304 to move relative to one another. Preferably, the support members 4322 provide a restricted range of motion, so as to provide stability and durability to the stem 4306 while still allowing the bulb 4302 and bulb 4304 to move relative to each other. For example, the support members 4322 may limit the motion to be in a single plane of motion.

When the device 4300 is in its resting state, the stem 4306 is straight, similar to the stem 4006 in FIG. 41. When the second bulb 4304 is inserted into the ear, however, the stem 4306 can bend as shown in FIG. 43. This allows the second bulb 4304 to follow the natural bend of the ear canal upon insertion. This provides improved comfort for the patient, and increases the ability to direct the flow of liquid medication into the correct location in the patient's ear.

Figure 44:
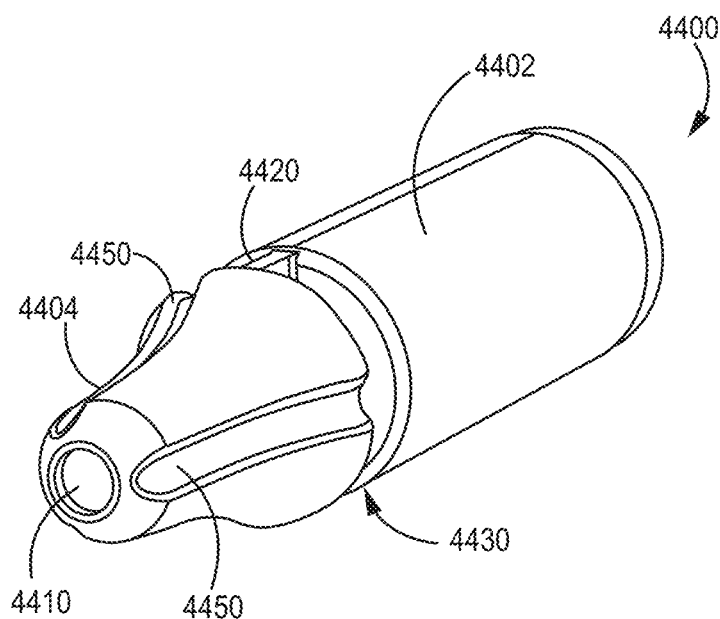
FIG. 44 is a perspective view of a device for dispensing medication, according to an embodiment.

FIG. 44 is perspective view of a device for dispensing medication, according to an alternative embodiment. The body of the device may be similar to that described in connection with FIGS. 40-43, however, the embodiment disclosed in FIG. 44 is not so limited.

The device 4400 has a first hollow bulb 4402 and a second hollow bulb 4404 which are connected by a hollow stem, similar to the stem 4006 of FIGS. 40-42. The hollow stem allows fluid, such as liquid or air, to pass from the first hollow bulb 4402 into the second hollow bulb 4404 when the first bulb 4402 is compressed. The device 4400 may include support members 4420 that span a gap 4430 between the first bulb 4402 and second bulb 4404.

Inserting liquid medication into a patient's ear can cause the air pressure in the ear to increase. This happens, for example, when air is not allowed to enter or exit the ear canal when inserting the liquid. The liquid displaces the volume of air in the ear canal, increasing the air pressure. This can cause discomfort to the patient, and even potential damage to the ear drum.

To prevent the increase of air pressure inside the patient's ear when liquid is propelled out of the tip 4410 of the bulb 4400 into the ear canal, the bulb 4404 has one or more grooves 4450 along the outside surface of the bulb 4404. The grooves 4450 extend along the bulb 4404 between the gap 4430 and the tip 4410 of the bulb 4404. The grooves 4450 of FIG. 44 are substantially straight, without curvature. The grooves prevent the device 4400 from creating an airtight seal when the second bulb 4404 is inserted into a patient's ear canal. Air can flow freely in and out of the ear canal through the grooves. When liquid is propelled into the patient's ear canal through the tip 4410 of the second bulb 4404, the liquid displaces air within the ear canal, but the air can escape through the grooves 4450. Thus the grooves 4450 regulate the air pressure in the ear canal. This allows for greater propulsion of liquid into the ear canal, and more effective delivery of liquid medication.

Figure 45:
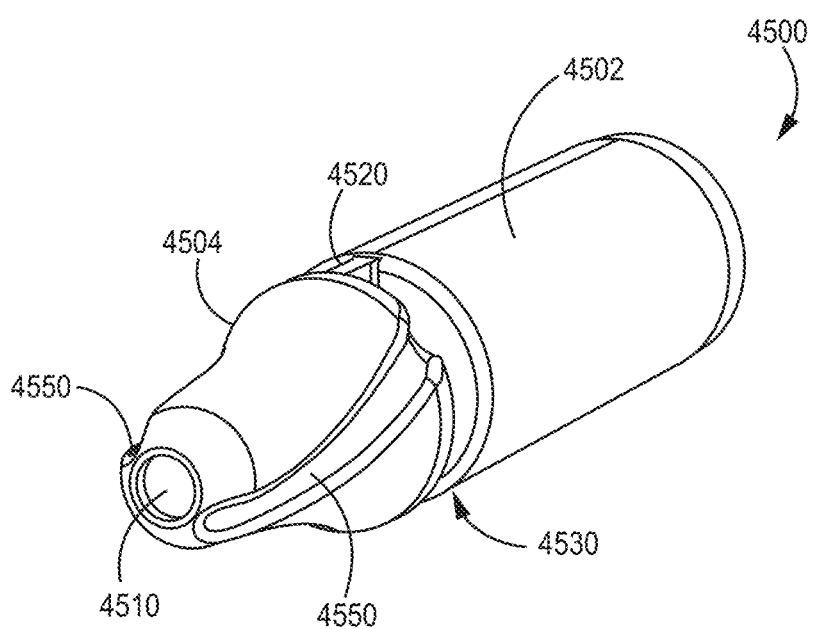
FIG. 45 is a perspective view of a device for dispensing medication, according to an embodiment.

FIG. 45 is perspective view of a device 4500 for dispensing medication, according to an alternative embodiment. Like the device 4400, the device 4500 has a first hollow bulb 4502, second hollow bulb 4504, a hollow stem connecting the bulbs 4502, 4504, optional support member 4520, and a gap 4530 between the first bulb 4502 and second bulb 4504. Device 4500 also has grooves 4550 extending from the gap 4530 toward the tip 4510 of the second bulb 4504. In the embodiment of FIG. 45, the grooves 4550 are not straight, but are curved slightly in a helical direction around the axis of the second bulb 4504. The grooves 4550 regulate air pressure in the ear canal in a similar manner to the grooves 4450 in the embodiment of FIG. 44. Because the groove

4550 is curved helically around the surface of the second bulb 4504, the cross-sectional area available for passage of air into and out of the ear canal is slightly increased compared to the straight groove 4450.

Figure 46:
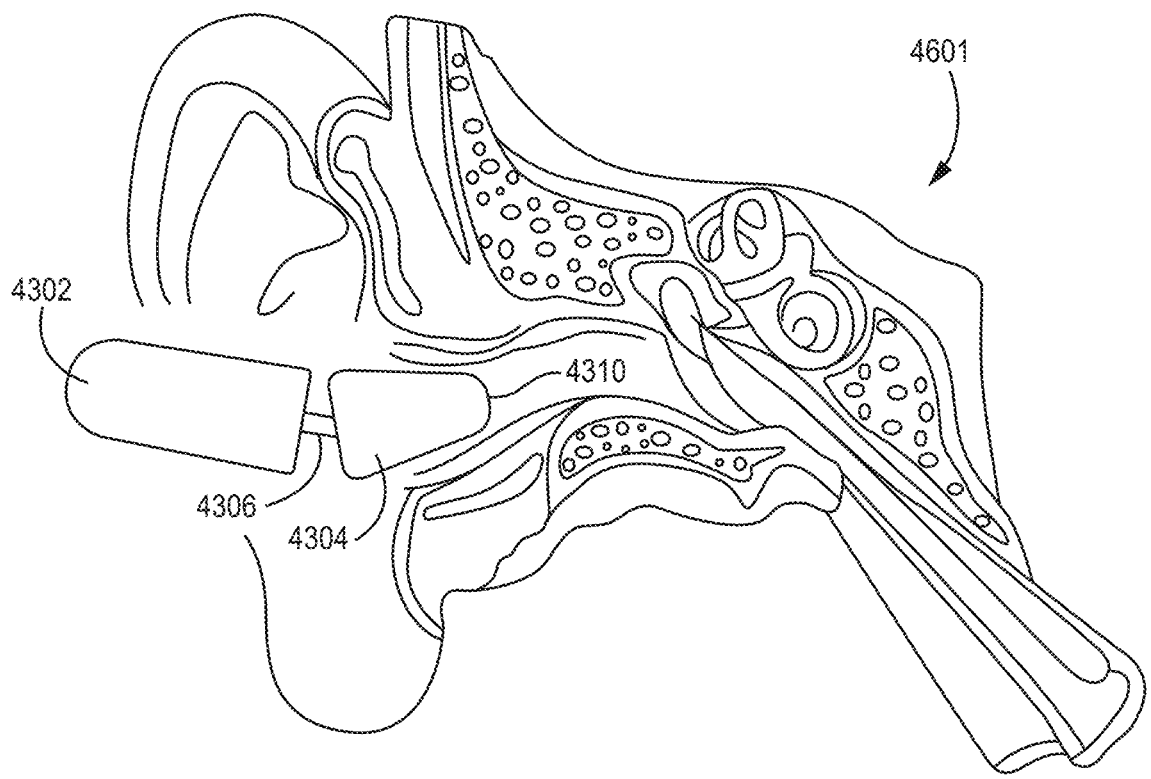
FIG. 46 demonstrates the device 4300 being inserted into a patient's ear canal 4601.

FIG. 46 demonstrates the device 4300 being inserted into a patient's ear canal 4601.

Figure 47A:
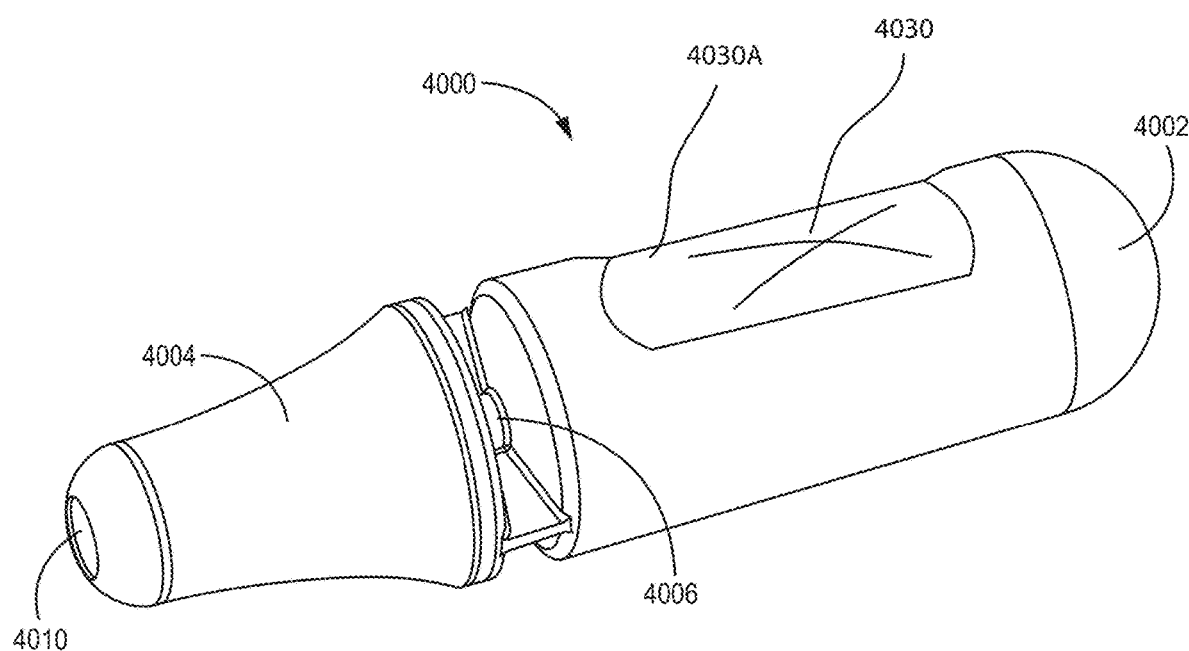
FIG. 47A is a perspective view of a device for dispensing medication, according to an embodiment, with an x-shaped fill port.

FIG. 47A is a perspective view of a device for dispensing medication, according to an embodiment. The device has a first hollow bulb 4002 and a second hollow bulb 4004 connected by a hollow stem 4006. The second hollow bulb has an opening 4010 at one end to allow fluid flow out of the bulb 4004. Both the bulb 4002 and bulb 4004 have openings connected to hollow stem 4006 such that the first bulb 4002 and second bulb 4004 are in fluid communication via stem 4006.

Fluids such as air or liquid can pass from one bulb to the other bulb through stem 4006. The second bulb 4002 is filled with a liquid by way of fill port 4030. In the embodiment shown the fill port 4030 has an X-shape, allowing for insertion of a tip of a bottle into the bulb 4002, but also providing resistance to fluid flow back out through the fill port 4030. Generally a finger is placed over fill port 4030 when administering fluids so as to prevent the fluid from flowing back out of bulb 4002, and to allow pressure to develop in the second bulb 4002 to propel fluids through the second bulb 4004 and out the tip 4010. The fill port 4030 is optionally a raised or protruding area of the bulb 4002. In the depicted example embodiment the fill port 4030 is shown in a recessed area 4030A, this recessed area 4030A has a benefit of making it easier for a medical professional to locate the fill port 4030 tactually (such as by rolling the device between their fingers once medicine has been added, without looking at the device, thereby allowing them to make sure they have covered the fill port 4030 with their finger when pinching the device to administer the medication).

Figure 47B:
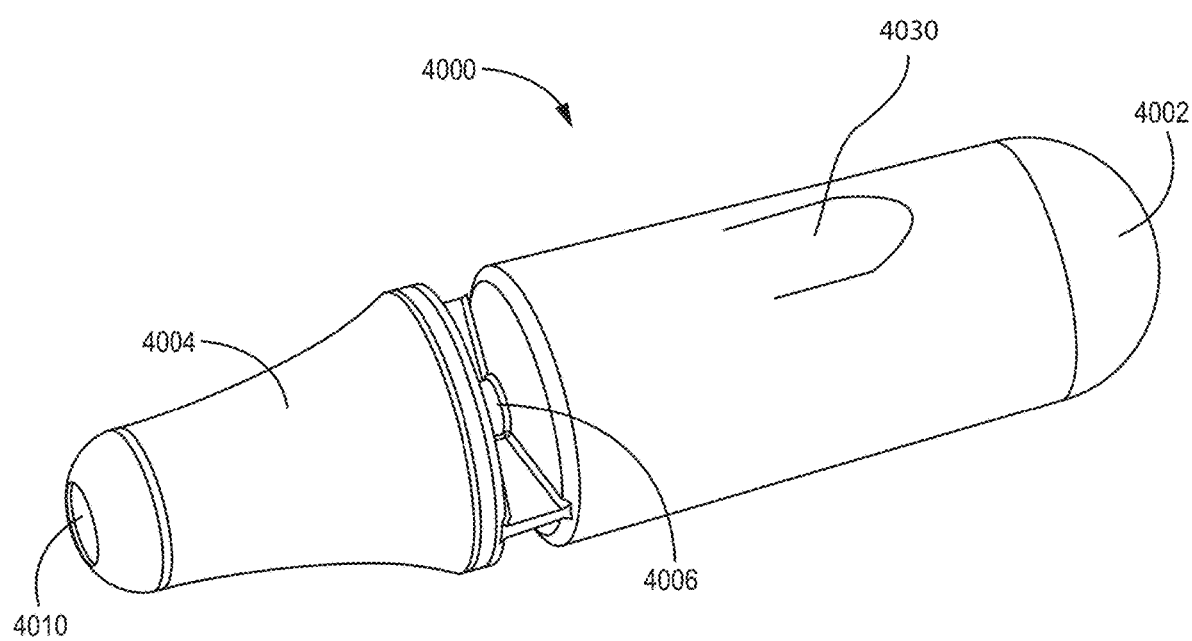
FIG. 47B is a perspective view of a device for dispensing medication, according to an embodiment, with a u-shaped fill port.

FIG. 47B is a perspective view of a device for dispensing medication, according to an embodiment. The device has a first hollow bulb 4002 and a second hollow bulb 4004 connected by a hollow stem 4006. The second hollow bulb has an opening 4010 at one end to allow fluid flow out of the bulb 4004. Both the bulb 4002 and bulb 4004 have openings connected to hollow stem 4006 such that the first bulb 4002 and second bulb 4004 are in fluid communication via stem 4006. Fluids such as air or liquid can pass from one bulb to the other bulb through stem 4006. The second bulb 4002 is filled with a liquid by way of fill port 4030. In the embodiment shown the fill port 4030 has a U-shape, allowing for insertion of a tip of a bottle into the bulb 4002, but also providing resistance to fluid flow back out through the fill port 4030. Generally a finger is placed over fill port 4030 when administering fluids so as to prevent the fluid from flowing back out, and to allow pressure to develop in the second bulb 4002 to propel fluids through the second bulb 4004 and out the tip 4010.

Figure 47C:
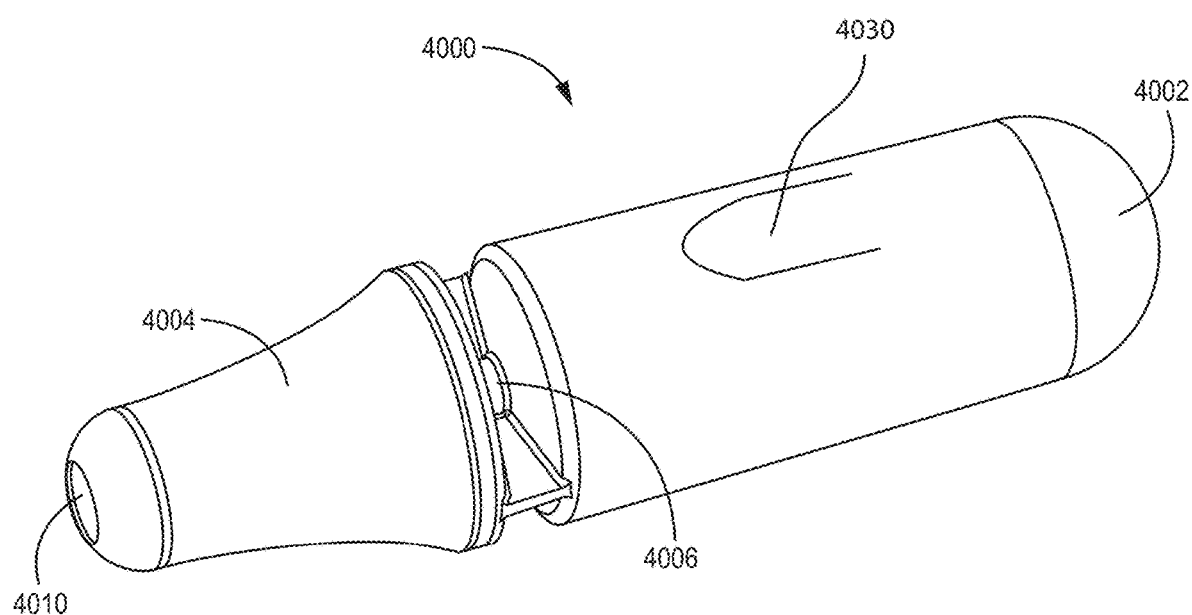
FIG. 47C is a perspective view of a device for dispensing medication, according to an embodiment, with a u-shaped fill port.

FIG. 47C is a perspective view of a device for dispensing medication, according to an embodiment. The device has a first hollow bulb 4002 and a second hollow bulb 4004 connected by a hollow stem 4006. The second hollow bulb has an opening 4010 at one end to allow fluid flow out of the bulb 4004. Both the bulb 4002 and bulb 4004 have openings connected to hollow stem 4006 such that the first bulb 4002 and second bulb 4004 are in fluid communication via stem 4006. Fluids such as air or liquid can pass from one bulb to the other bulb through stem 4006.

The bulb 4002 is filled with a liquid by way of fill port 4030. In the embodiment shown the fill port 4030 has an U-shape, opposite to the one shown in FIG. 47B, allowing for insertion of a tip of a bottle into the bulb 4002, but also providing resistance to fluid flow back out through the fill port 4030. Generally a finger is placed over fill port 4030 when administering fluids so as to prevent the fluid from flowing back out, and to allow pressure to develop in the second bulb 4002 to propel fluids through the second bulb 4004 and out the tip 4010.

Figure 47D:
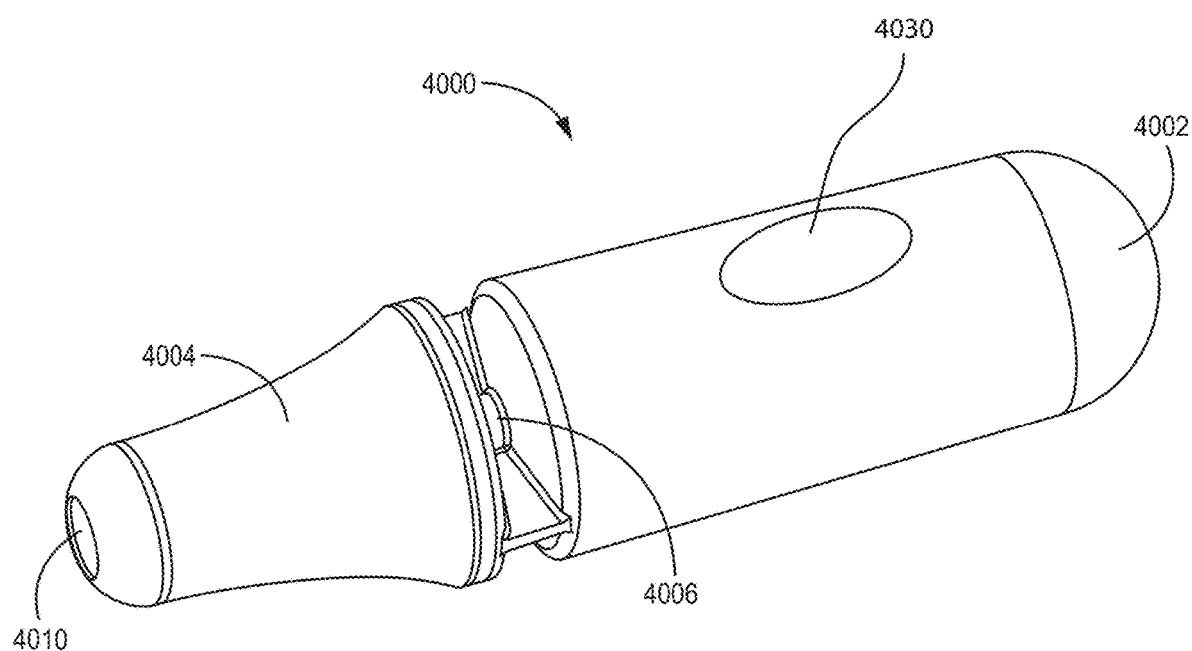
FIG. 47D is a perspective view of a device for dispensing medication, according to an embodiment, with an open fill port.

FIG. 47D is a perspective view of a device for dispensing medication, according to an embodiment. The device has a first hollow bulb 4002 and a second hollow bulb 4004 connected by a hollow stem 4006. The second hollow bulb has an opening 4010 at one end to allow fluid flow out of the bulb 4004. Both the bulb 4002 and bulb 4004 have openings connected to hollow stem 4006 such that the first bulb 4002 and second bulb 4004 are in fluid communication via stem 4006. Fluids such as air or liquid can pass from one bulb to the other bulb through stem 4006. The second bulb 4002 is filled with a liquid by way of fill port 4030. In the embodiment shown the fill port 4030 has opening allowing for insertion of a tip of a bottle into the bulb 4002. Generally a finger is placed over fill port 4030 when administering fluids so as to prevent the fluid from flowing back out, and to allow pressure to develop in the bulb 4002 to propel fluids through the bulb 4004 and out the tip 4010.

Figure 47E:
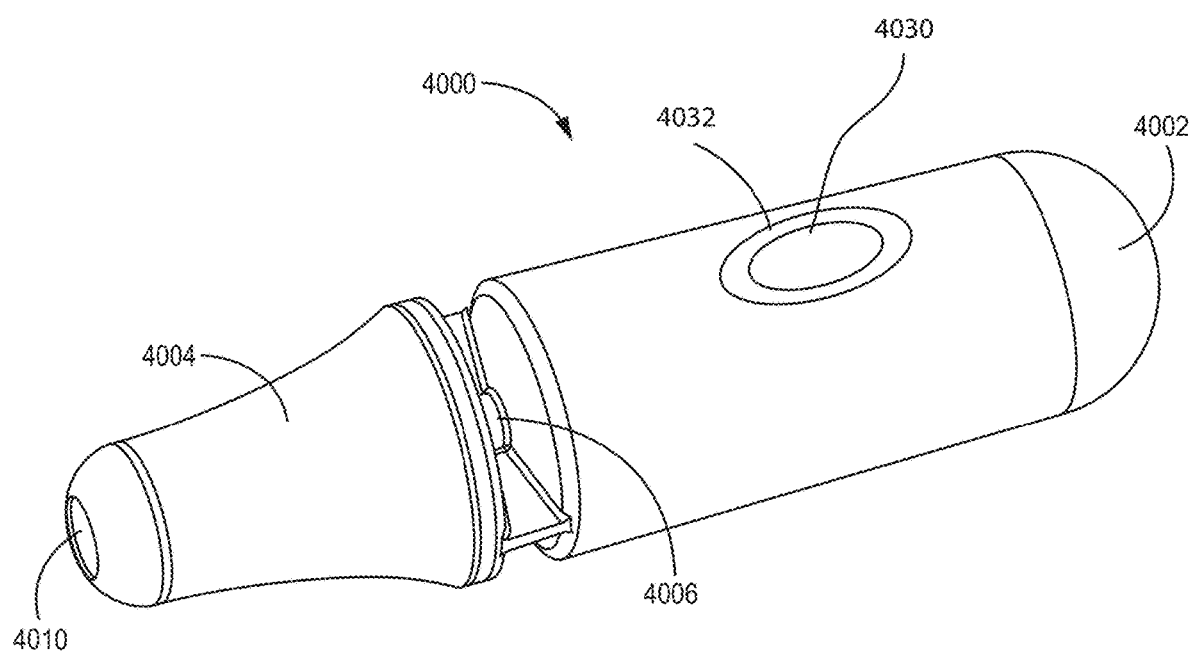
FIG. 47E is a perspective view of a device for dispensing medication, according to an embodiment, with a fill valve.

FIG. 47E is a perspective view of a device for dispensing medication, according to an embodiment. The device has a first hollow bulb 4002 and a second hollow bulb 4004 connected by a hollow stem 4006. The second hollow bulb has an opening 4010 at one end to allow fluid flow out of the bulb 4004. Both the bulb 4002 and bulb 4004 have openings connected to hollow stem 4006 such that the first bulb 4002 and second bulb 4004 are in fluid communication via stem 4006. Fluids such as air or liquid can pass from one bulb to the other bulb through stem 4006.

The bulb 4002 is filled with a liquid by way of fill port 4030. In the embodiment shown the fill port 4030 has valve 4032, shown in simplified form such as a silicone valve allowing for insertion of a tip of a bottle into the bulb 4002, but also preventing fluid flow back out through the fill port. Generally a finger is placed over fill port 4030 when administering fluids so as to prevent the fluid from flowing back out, and to allow pressure to develop in the second bulb 4002 to propel fluids through the bulb 4004 and out the tip 4010.

Figure 48A:
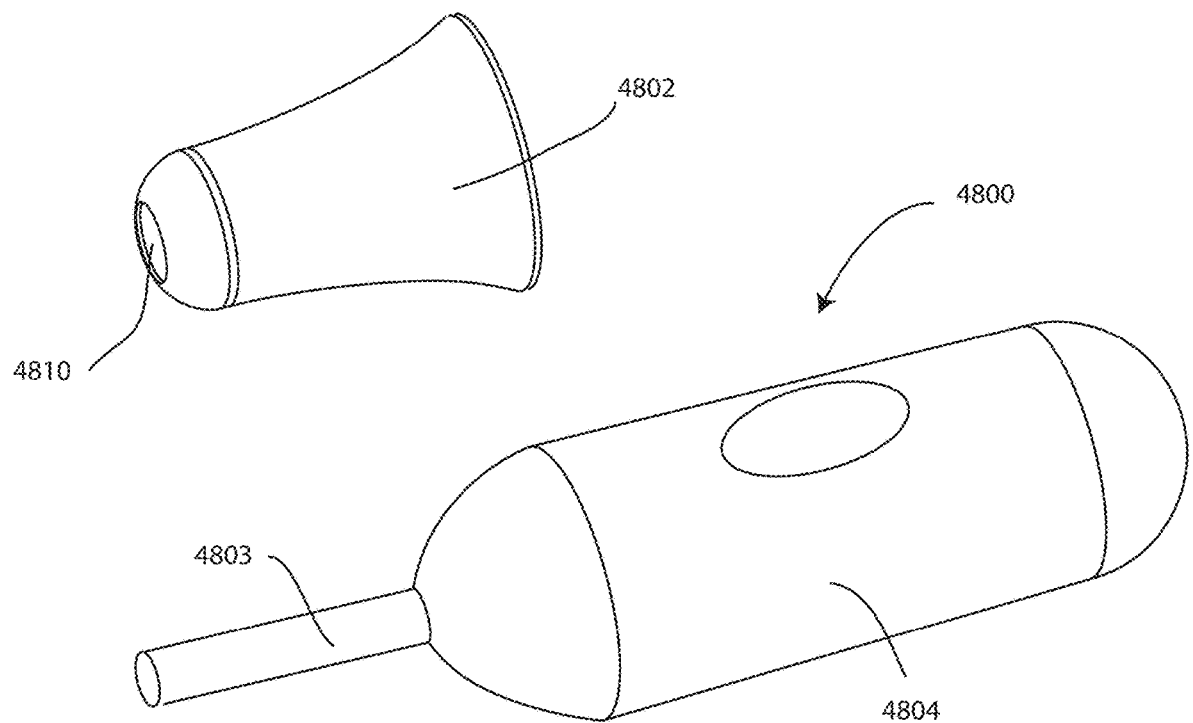
FIG. 48A is a perspective view of a device for dispensing medication according to an embodiment, the device comprising a two part design, the two parts shown separated.
Figure 48B:
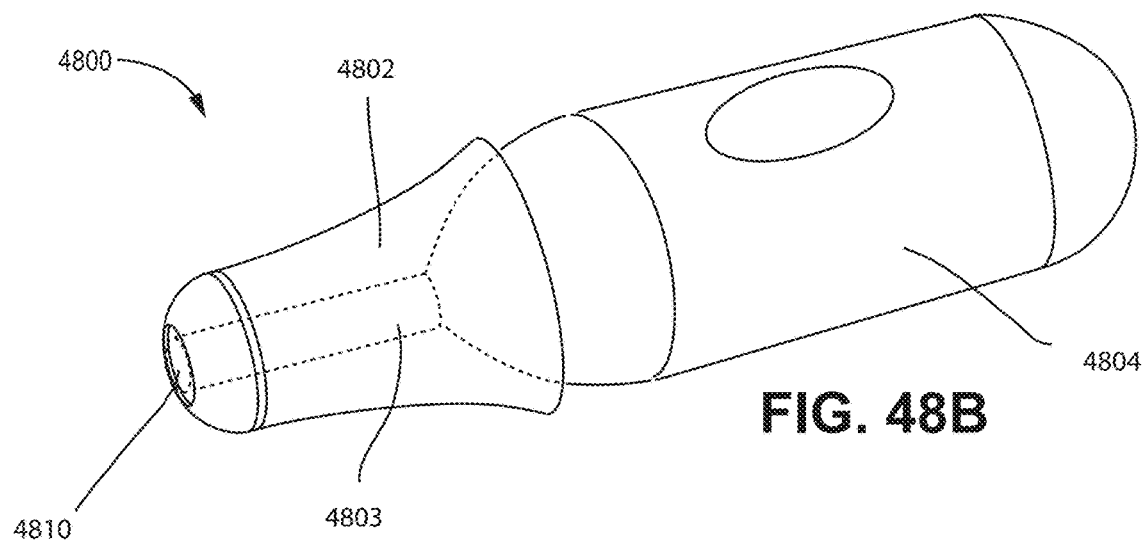
FIG. 48B is a perspective view of a device for dispensing medication according to an embodiment, the device comprising a two part design, the two parts shown joined together.

FIG. 48A is a perspective view of a device for dispensing medication according to an embodiment, the device comprising a two part design, the two parts shown separated. The design includes a sheath 4802 plus a bulb 4804. Bulb 4804 also includes an elongate exit tube 4803. These parts are shown combined in FIG. 48B. The sheath 4802 that is applied over the exit tube 4803 and secured in place with a glue or with an interlocking male/female features. The exit tube 4803 can optionally have a much smaller diameter than the opening 4810 on the sheath. A smaller tip help atomizes drops and helps propel drops more with added velocity, potentially increasing ear drop dose delivery. The tip of the sheath 4802 can be of varying lengths and inner/outer diameters. The inner diameter of the exit tube 4803 can optionally be no less than 1 mm to make gas sterilization at a hospital/surgery center easy and affordable. The inner diameter of exit tube 4803 can be as small as 0.2 mm in other implementations, such as for sterilization by radiation. The diameter of the opening 4810 in the sheath can be much larger, such as 7 mm. The tip length of the exit tube 4803 can be varied, such as 1 mm to 30 mm. In some implementations it extends outside of the opening 4810 of the sheath 4802.

Typically there is a gap between the sheath 4802 and the end of the bulb 4804 to allow for pivoting of the sheath 4802 and 4804 relative to one another. The length is typically not so long as to touch the ear drum, thus avoiding trauma to the ear drum. The tip can be of material soft enough (low density polyethylene) and would have rounded edges to avoid discomfort or trauma to the ear canal skin. This tip helps aid in getting drops even further in the ear canal of the smallest ear canals, (the vented and conical shape portion of the device assure no one could insert the thin tip far enough to reach the ear drum). In some implementations a locking mechanism on exit tube 4803 can fit into a female portion of the sheath 4802 to secure the exit tube 4803 and sheath 4802 together. Optionally the sheath 4802 will have a hollow shaft that is just larger than the stem of exit tube 4803.

Figure 49:
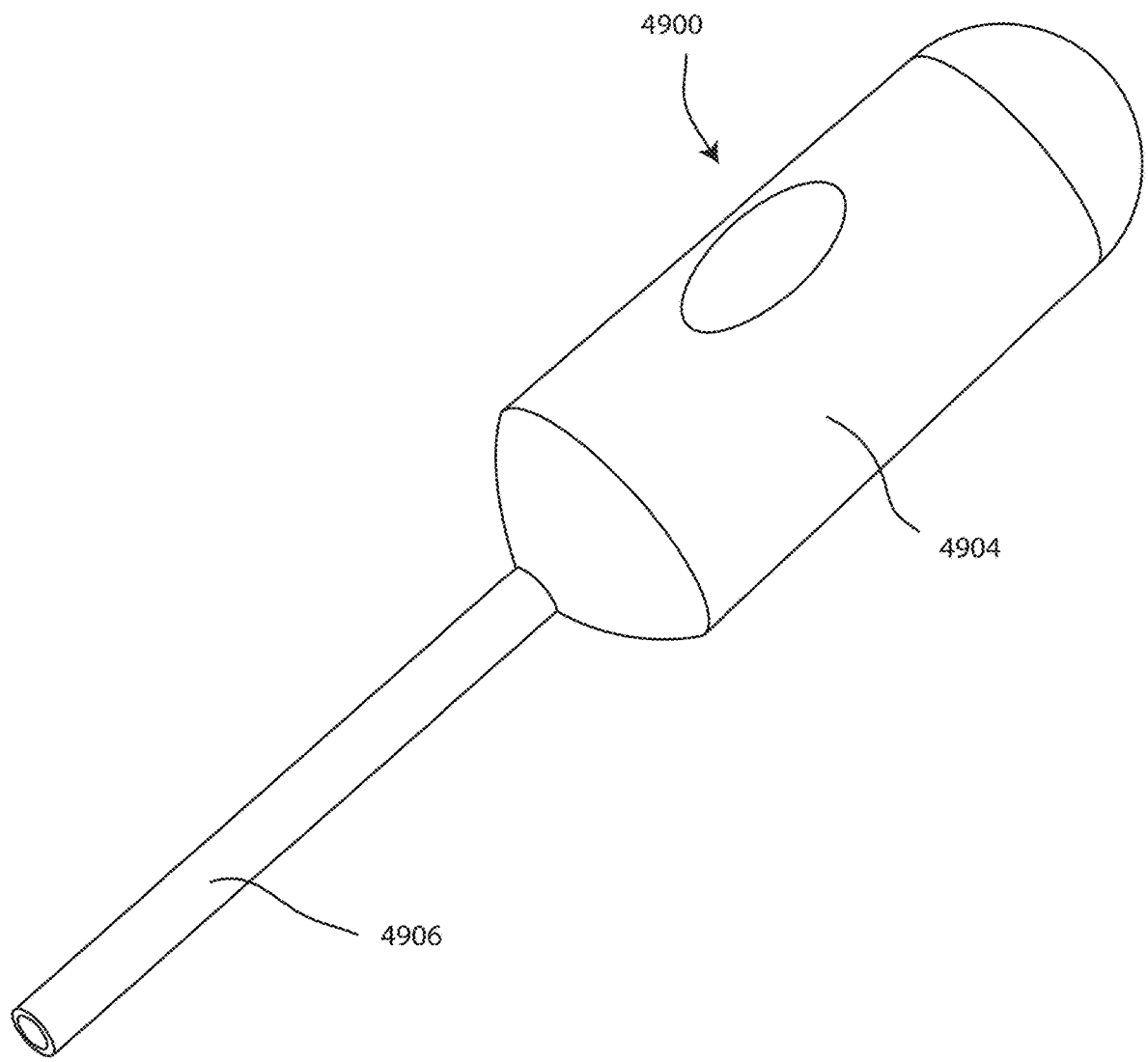
FIG. 49 is a perspective view of a device for dispensing medication, according to an embodiment, with an elongate tip.

FIG. 49 is a perspective view of a device 4900 for dispensing medication, according to an embodiment, with an elongate tip 4906. The elongated tip 4906 is long enough to go through a hole (myringotomy, perforation, ear tube) so that medicine can be applied directly into the middle ear. This attribute is useful in some embodiments for delivering drugs (such as Otiprio) that are administered as a delayed release drug—via a syringe and long needle—directly into the middle ear. The drops with this long tip can be administered directly by a doctor under aid of an operating microscope.

Figure 50:
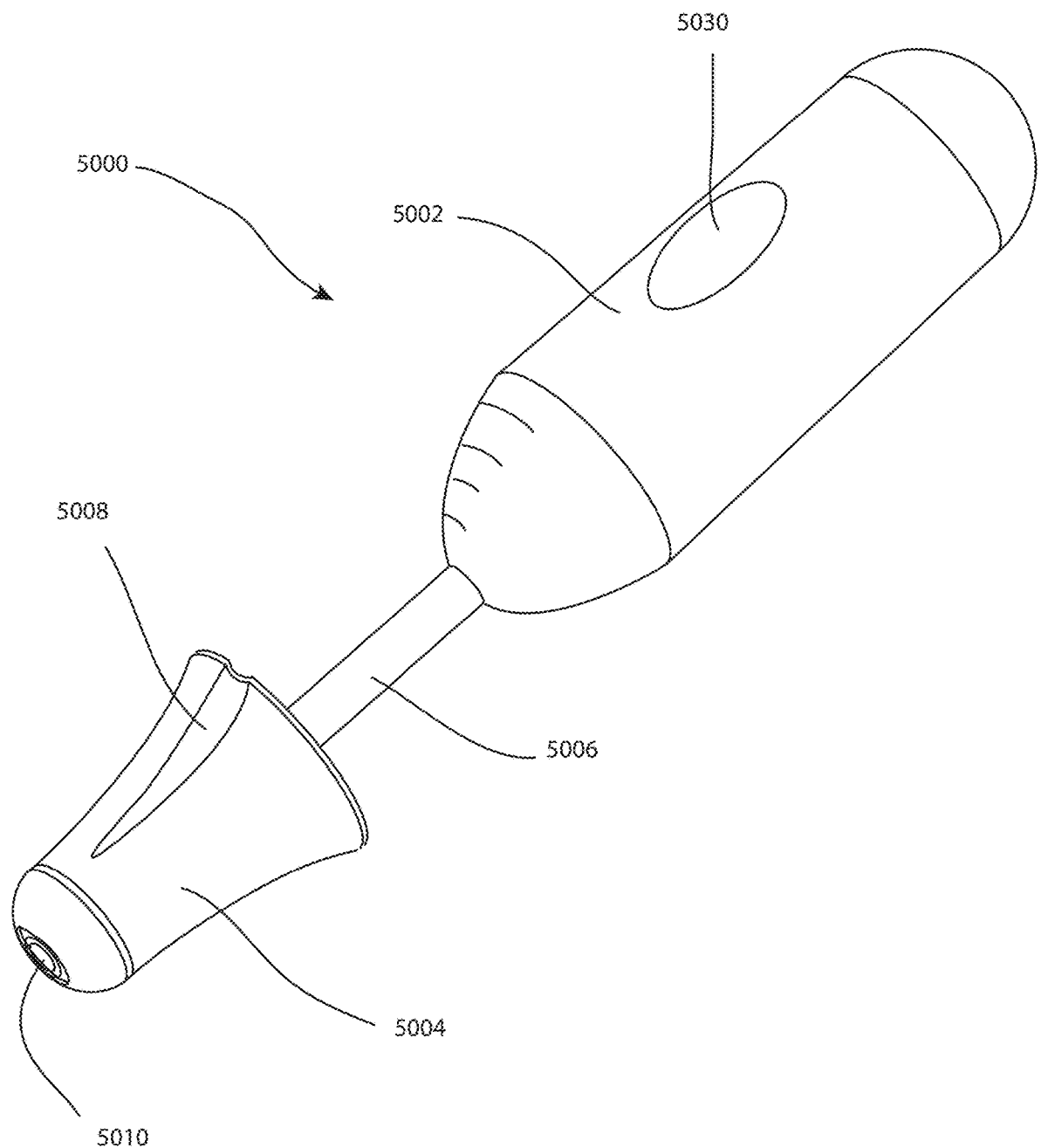
FIG. 50 is a perspective view of a device for dispensing medication according to an embodiment.

FIG. 50 is a perspective view of a device 5000 for dispensing medication. The device has a first hollow bulb 5002 and a second hollow bulb 5004 connected by an elongate hollow stem 5006. The second hollow bulb has an opening 5010 at one end to allow to fluid flow out of the bulb 5004. Both the bulb 5002 and bulb 5004 have openings connected to hollow stem 5006 such that the first bulb 5002 and second bulb 5004 are in fluid communication via stem 5006.

Fluids such as air or liquid can pass from one bulb to the other bulb through stem 5006. Liquid medication is added to second bulb 5002 by way of fill port 5030. In the embodiment shown the fill port 5030 has an oval opening, allowing for insertion of a tip of a bottle into the bulb 5002. Generally a finger is placed over fill port 5030 when administering fluids so as to prevent the liquid medication from flowing back out of bulb 5002, and to allow air pressure to develop in the first bulb 5002 to propel fluids through the second bulb 5004 and out the tip 5010. The fill port 5030 is optionally a raised or protruding area of the bulb 5002.

Figure 51:
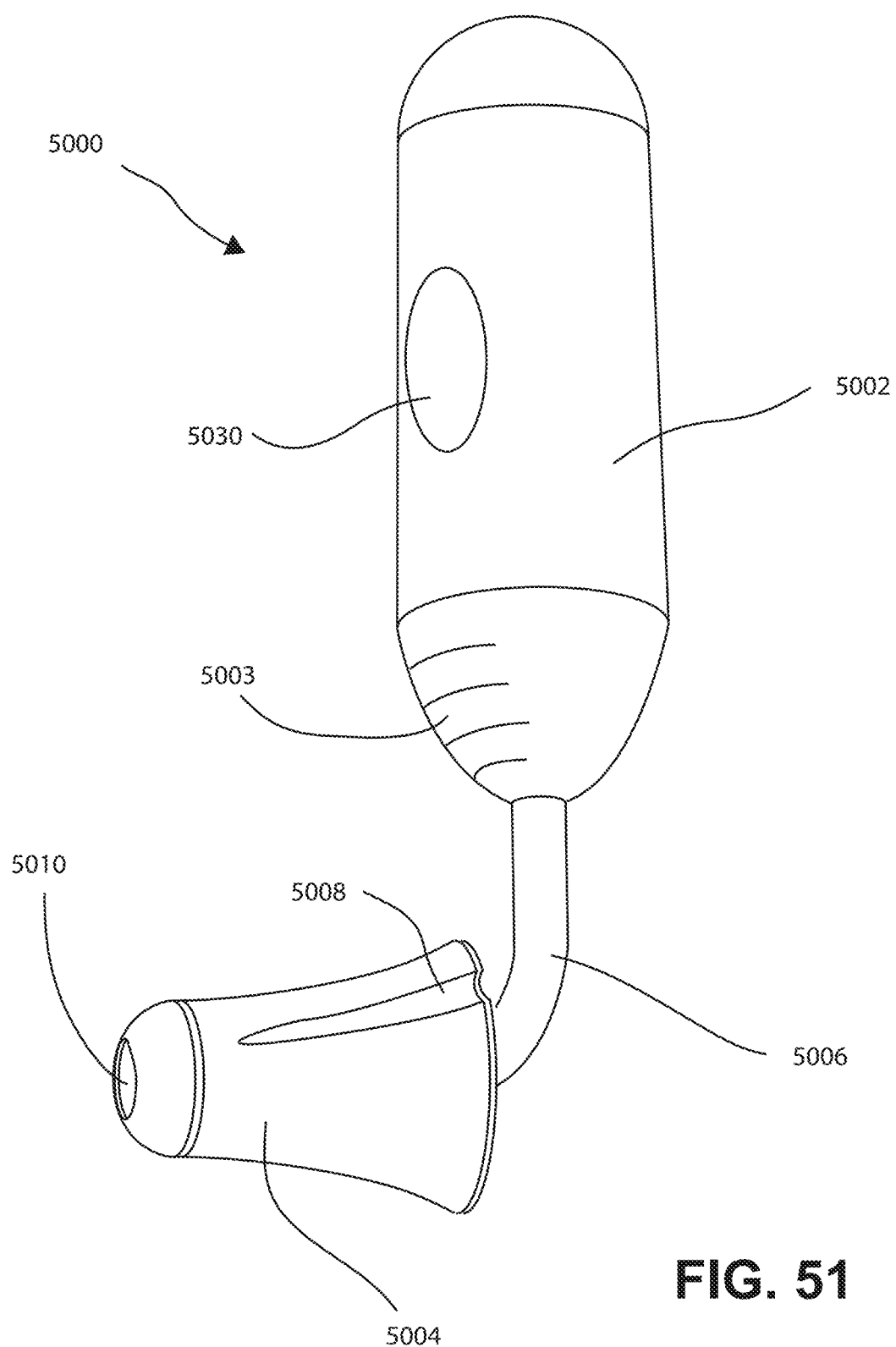
FIG. 51 is a perspective view of the device for dispensing medication according to FIG. 50, showing the tip bent for insertion into a patient's outer ear.

FIG. 51 is a perspective view of the device 5000 for dispensing medication according to FIG. 50, showing the end bent for insertion of the second bulb 5005 into a patient's outer ear. Also shown is a vent 5008 in the second bulb 5004. These vents 5008 are such that insertion of the second bulb 5004 into a patient's outer ear does not create an air tight seal. As a result, excess pressure does not build up inside the ear when air and medicine is directed into the ear by contraction of first bulb 5002, even when that contraction of bulb 5002 is rapid and forceful. The ability of the first and second bulbs to move freely with regard to orientation of each other allows for application of medication into the inner ear without having the patient tilt his or head until the ear canal is pointing upright as is necessary with standard ear drops.

Figure 52:
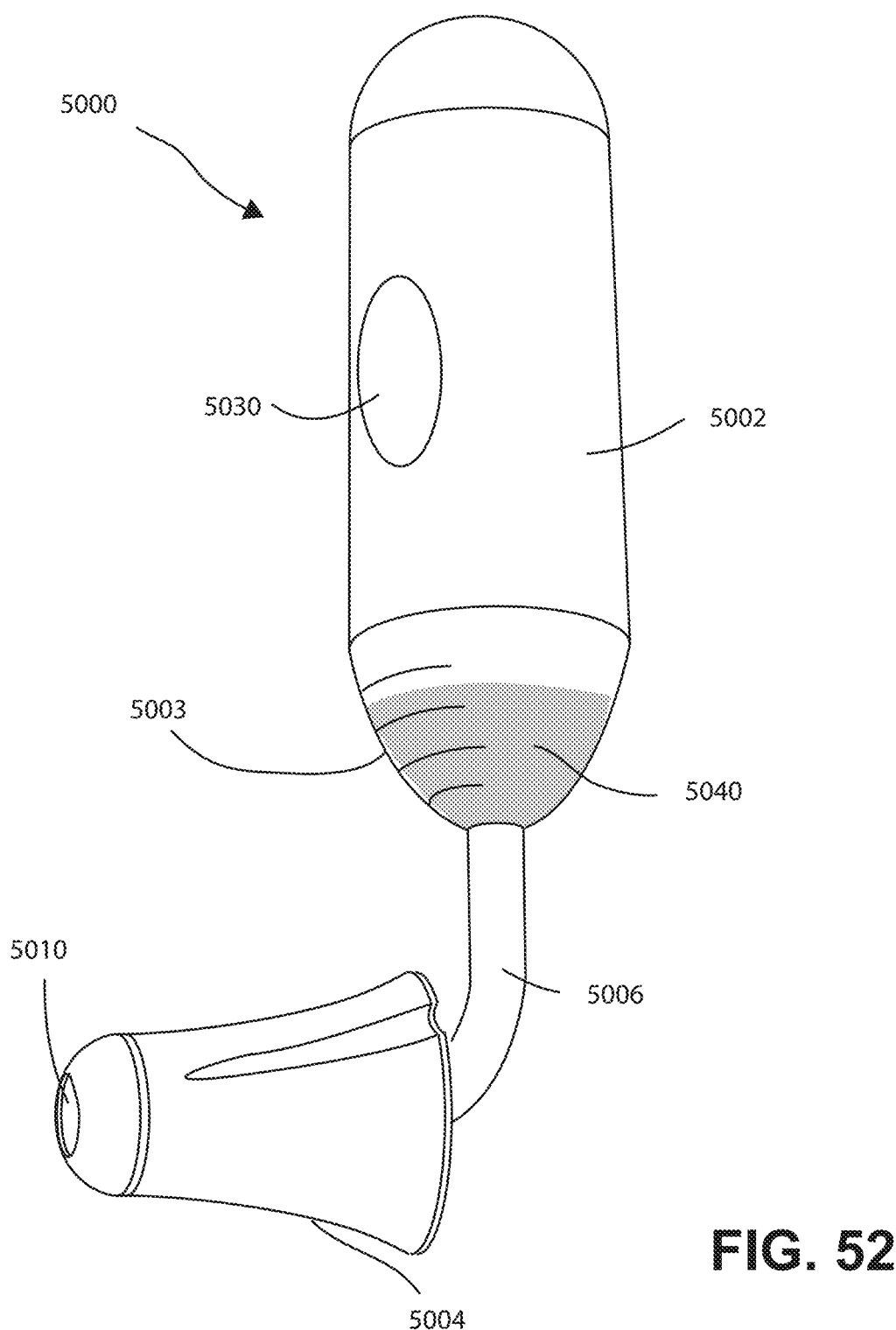
FIG. 52 is a perspective view of the device for dispensing medication according to FIG. 50, showing the tip bent for insertion into a patient's outer ear, and with medication collecting in the upper portion.

Benefits of this improved design can be seen in FIG. 52, which is a perspective view of the device 5000 for dispensing medication according to FIG. 50, showing the tip bent for insertion of the end of the second bulb 5004 into a patient's outer ear, and with medication 5040 collecting in the bottom 5003 of the first bulb 5002. The bottom 5003 of the first bulb 5002 has a tapered end leading into the hollow stem 5006. This tapered bottom 5003 is beneficial because it allows medication to collect in a small space leading directly into the hollow stem 5006 so that upon compression of the first bulb 5002, the expulsion of air from the first bulb 5002 will propel the mediation through the stem 5006, through the second bulb 5004, and out the opening 5010. Indicia can be added to the bottom 5003 of the first bulb 5002 to measure medication.

Figure 53:
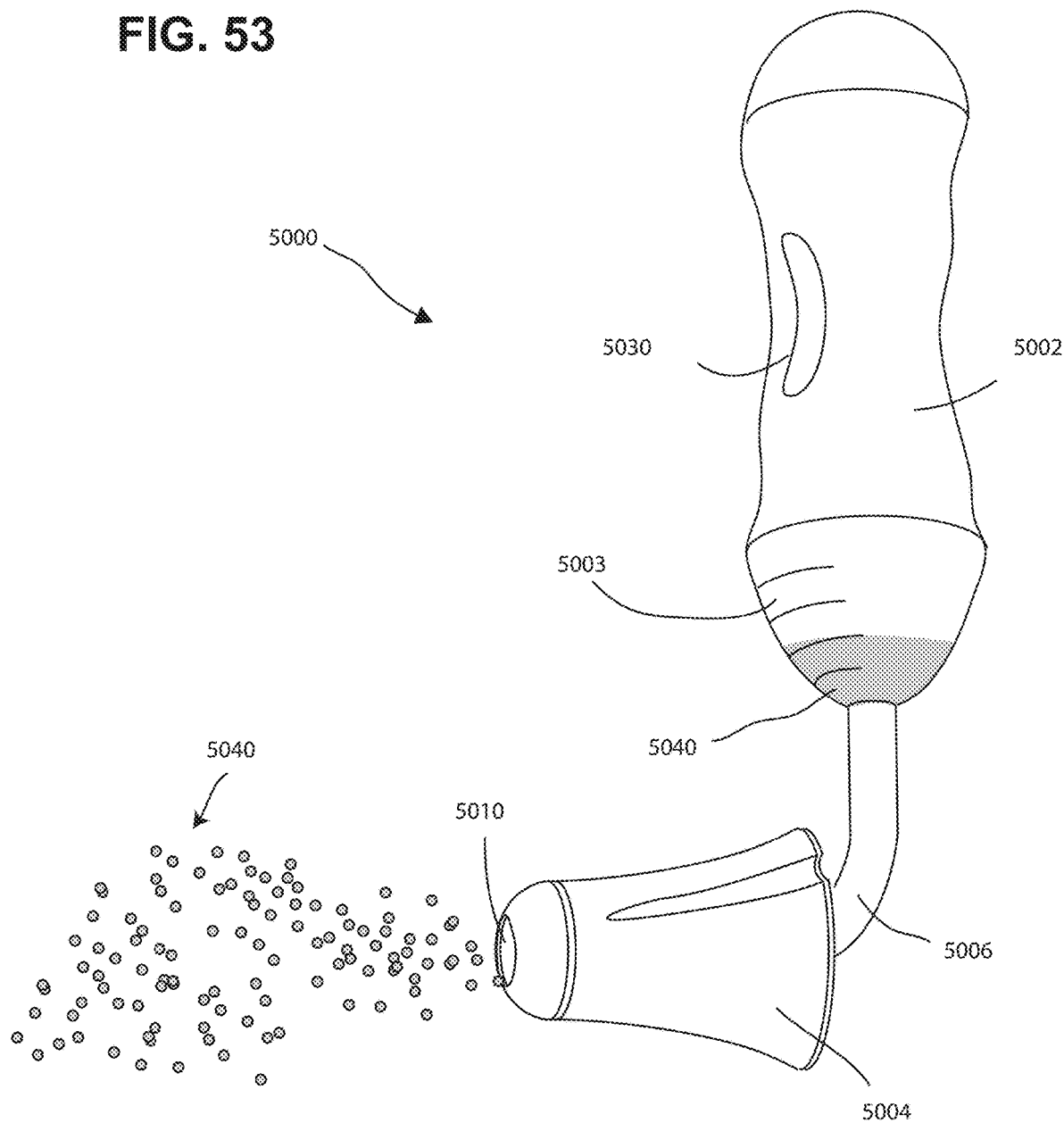
FIG. 53 is a perspective view of the device for dispensing medication according to FIG. 50, showing the tip bent for insertion into a patient's outer ear, and with medication starting to be dispensed.
Figure 54:
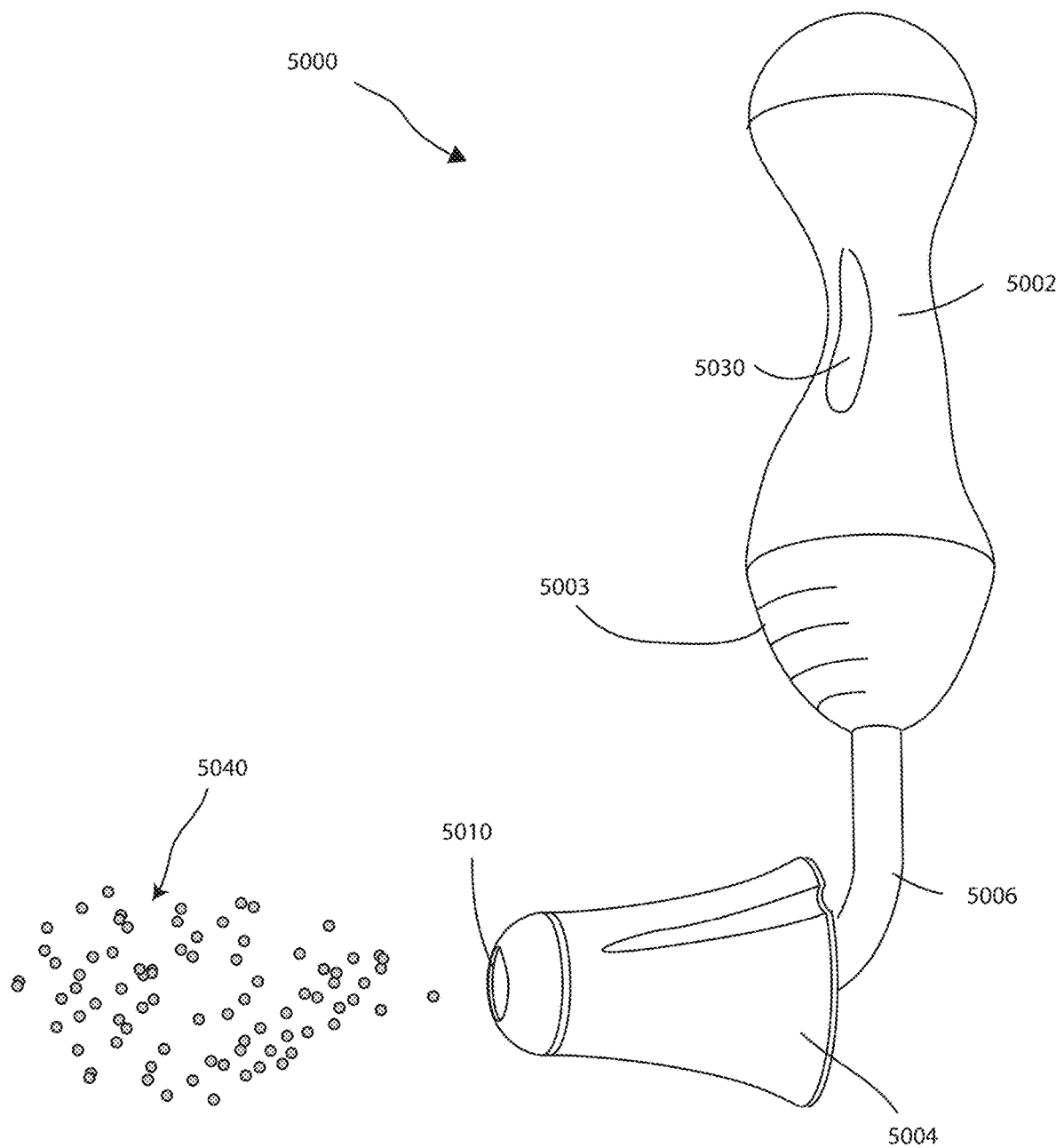
FIG. 54 is a perspective view of the device for dispensing medication according to FIG. 50, showing the tip bent for insertion into a patient's outer ear, and with medication continuing to be dispensed.

FIGS. 53 and 54 show the result of squeezing the first bulb 5002. In FIG. 53 the bulb 5002 is partially squeezed, with an initial volume of the medication 5040 having left the second bulb 5002, passed through the stem 5006 and second bulb 5004, and thereafter out the opening 5010. It will be observed that that in this manner the medication can be delivered horizontally out the device 5000, even while the top of the device 5000, in particular first bulb 5002, is kept vertical. FIG. 54 shows the remainder of the medication 5040 having been discharged as first bulb 5002 is further squeezed (opening 5030 would be covered so pressure can build up in bulb 5002).

Also, it will be observed that the present construction allows for the medication to be delivered in very small drops, much like a spray or mist, because typically a much greater amount of air is discharged than liquid. In this manner, the liquid is carried out by the air. The air pressure itself within the ear can be kept at a low differential to atmospheric air because, in part, of the relatively small volumes of air but also the venting provided by vent 5008 (see labeled vent in FIG. 50).

In an example implementation, approximately 1 mil of air is expelled from device 5000, while 0.1 mil of medication is discharged.

It will be understood that in some implementations the stem 5006 extends all the way through the second bulb 5004, and the stem 5006 terminates near the opening 5010 in the second bulb 5004. Thus, in some implementations medication passes through the interior of bulb 5004 without contacting the bulb. In this regard the bulb 5004 can be just a funnel-shaped addition to the device 5000, fitting over the end of the stem 5006.

Figure 55:
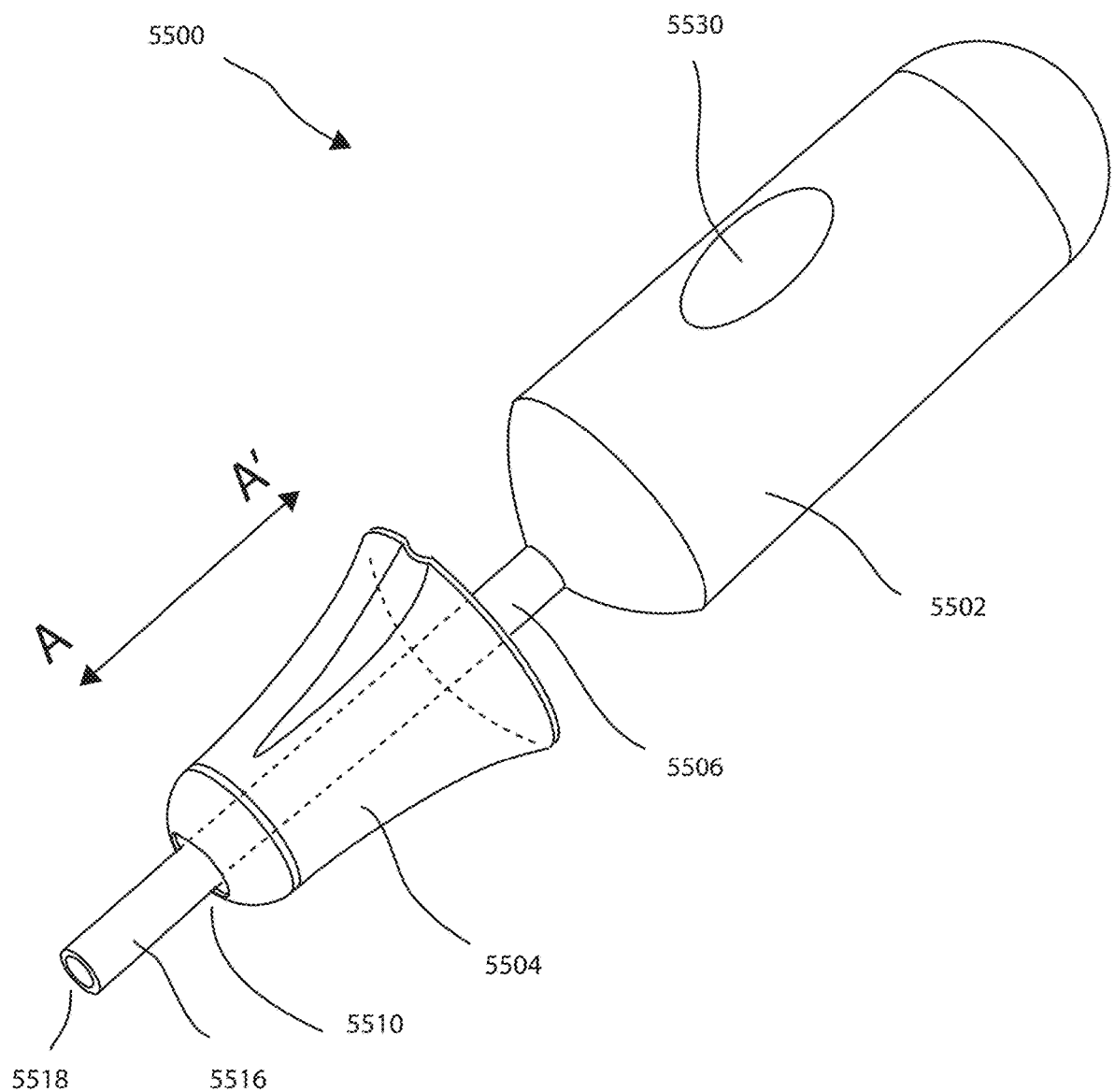
FIG. 55 is a perspective view of a device for dispensing medication, including a two part design with an end configured with a narrow end extension.

FIG. 55 is a perspective view of a device for dispensing medication, including a two-part design with an end configured with a narrow end extension. The device has a first hollow bulb 5502 and a second hollow bulb 5504 connected by an elongate hollow stem 5506. The second hollow bulb has an opening 5510 at one end to allow fluid flow out of the bulb 5504. Both the bulb 5502 and bulb 5504 have openings connected to hollow stem 5506 such that the first bulb 5502 and second bulb 5504 are in fluid communication via stem 5506. The second bulb 5504 can travel back and forth along the stem 5506 in the direction A=A', often to various set locations such as with notches, and as such the end 5518 at the tip 5516 of the stem 5506 can extend further beyond the opening 5510 at the second bulb 5504. Typically the end 5518 is a soft material. This configuration allows, for example, medication to be delivered deeper and with more focus into the inner ear, typically by a medical professional.

Figure 56:
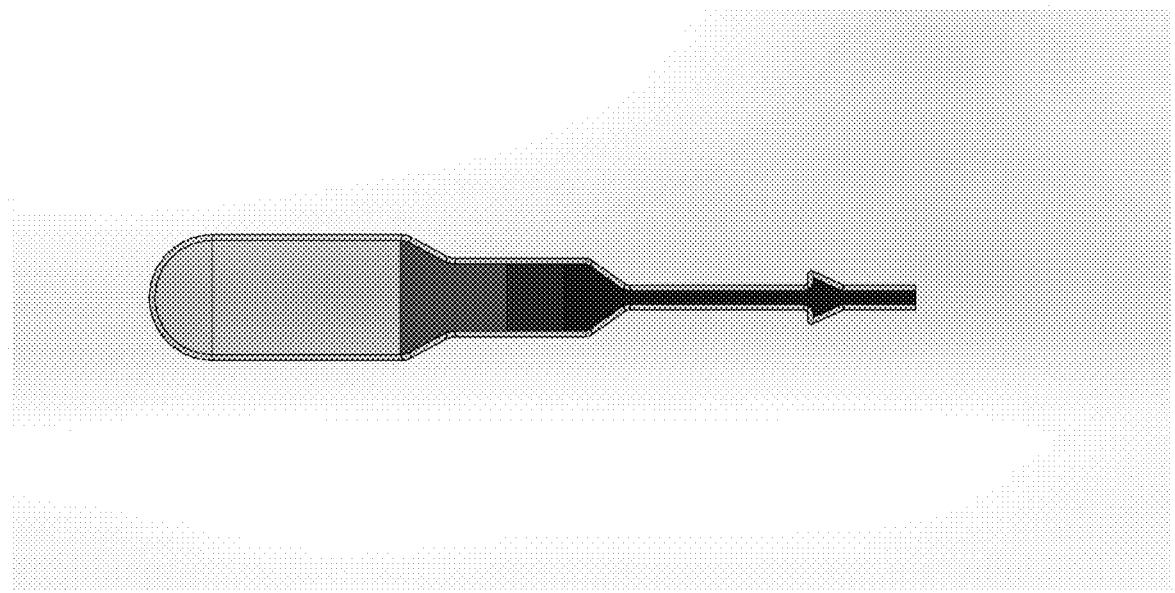
FIG. 56 is a perspective view of a device for dispensing medication, showing a device with gradations on the side.

FIG. 56 is a perspective view of a device for dispensing medication, showing a device with gradations on the side.

Figure 57:
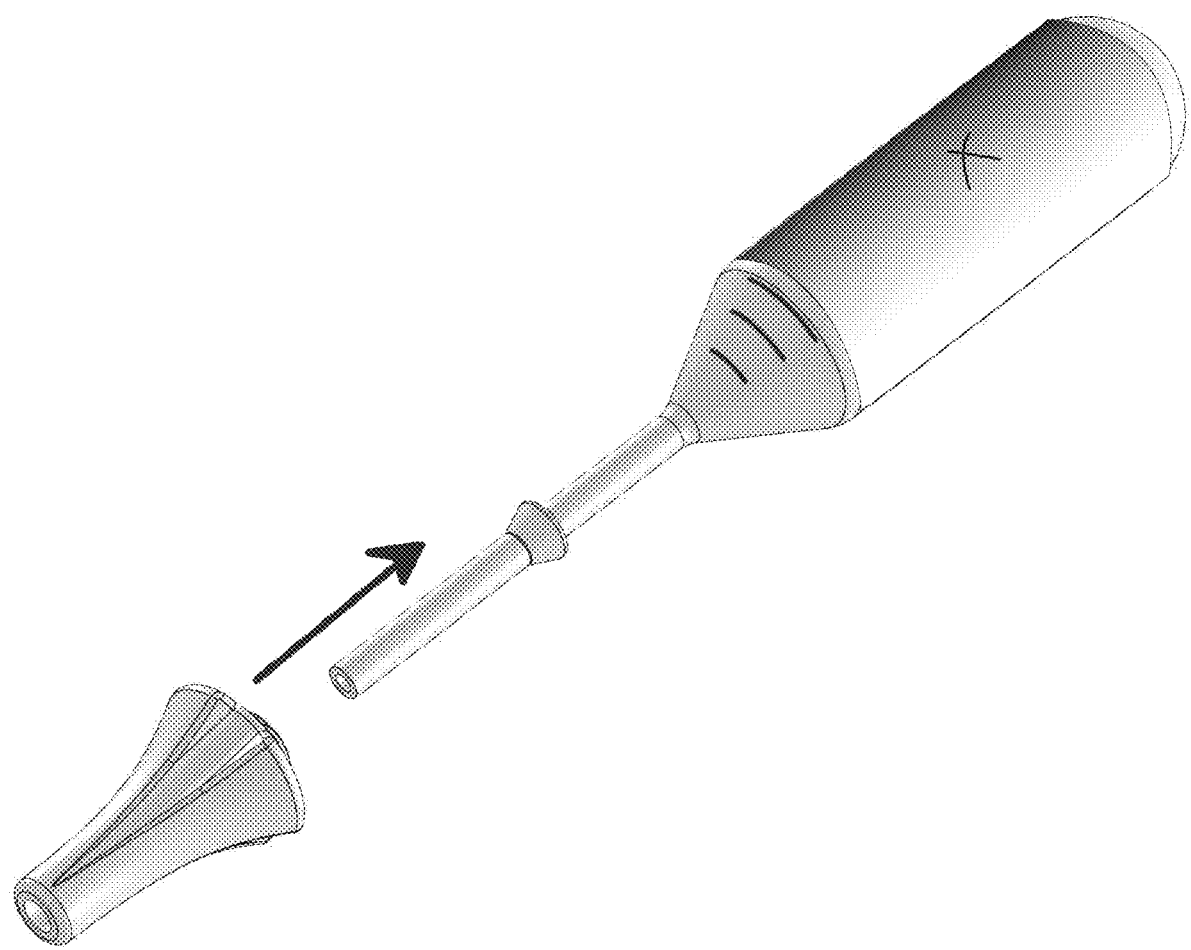
FIG. 57 is a perspective view of a device for dispensing medication, showing a two-part configuration with a removable tip and a connector for securing the tip to the rest of the dispenser.

FIG. 57 is a perspective view of a device for dispensing medication, showing a two-part configuration with a removable tip and a connector for securing the tip to the rest of the dispenser.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference.

The technology has been described with reference to various specific and preferred embodiments and techniques. However, it should be understood that many variations and modifications may be made while remaining within the spirit and scope of the technology.

The invention claimed is:

1. A device for the dispensing of liquids, comprising:
   a first hollow bulb, wherein the first hollow bulb is compressible; the first hollow bulb including a fill port in a side of the first hollow bulb for injecting liquid into the first hollow bulb, the fill port comprising at least one depressible portion covering a portion of the fill port, the depressible portion allowing for a liquid-containing nozzle to insert into the port such that the depressible portion depresses toward the interior of the of the first hollow bulb, the depressible portion returning to a non-depressed form after the liquid-containing nozzle is removed; the depressible portion not providing a full seal to the interior of the hollow bulb, but wherein a finger extending over the port provides a substantially-complete seal during compression of the first hollow bulb;
   a second hollow bulb the second hollow bulb comprising a tapered profile, further including a vent along the exterior of the second hollow bulb, the vent extending from near a first end of the second hollow bulb to a second end of the second hollow bulb, the vent comprising a recess in the second bulb allowing for air to pass out of an inner ear when liquid is injected into an ear by compression of the first hollow bulb; and
   a hollow stem comprising a first end and a second end, wherein the first hollow bulb is coupled to the first end and the hollow stem extends through the second hollow bulb and the second end of the hollow stem emerges from the second end of the second hollow bulb, the hollow stem providing a conduit through the second hollow bulb;
   wherein the second end of the hollow stem terminates at the distal end of the second hollow bulb;
   wherein the hollow stem is substantially rigid such that the first hollow bulb and second hollow bulb remain in a substantially straight alignment when not in use, but the hollow stem is flexible enough that it readily allows for creation of a 90 degree angle between the first and second hollow bulbs.

2. The device for the dispensing of liquids according to claim 1, wherein the second end of the hollow stem is tapered.

3. The device for the dispensing of liquids according to claim 1, wherein the first hollow bulb comprises volumetric indicia.

4. The device for the dispensing of liquids according to claim 1, wherein the first hollow bulb, second hollow bulb, and the hollow stem comprise a transparent polymer.

5. The device for the dispensing of liquids according to claim 1, wherein the stem has a circular cross-section.

6. The device for the dispensing of liquids according to claim 1, wherein the first bulb and the second bulb have circular cross-sections.

7. The device for the dispensing of liquids according to claim 1, wherein the first bulb has a length substantially equal to the length of the second bulb.

8. The device for the dispensing of liquids according to claim 1, wherein the length of the stem is greater than the length of the first bulb or the second bulb.

9. The device for the dispensing of liquids according to claim 1, wherein the device has a total length of at least 1 cm and not more than 10 cm.

10. The device for the dispensing of liquids according to claim 1, wherein the device is configured to discharge an amount of fluid that ranges from 0.5 ml to 5 ml.

11. A device for dispensing fluids, the device comprising:
    a compressible first hollow bulb;
    a second hollow bulb having a tapered bulb tip and a hollow interior;
    a conduit integrally formed with the first hollow bulb and passing from an end of the first hollow bulb through the second hollow bulb and through the hollow interior of the second hollow bulb, such that fluid travelling through the second hollow bulb only travels through the conduit and does not otherwise enter the hollow interior of the second hollow bulb; and
    a groove along the surface of the second hollow bulb, the groove extending from the bulb tips;
    wherein the second hollow bulb fits over the conduit integrally formed with the first hollow bulb, and the second hollow bulb is removable from the conduit.

12. The device of claim 11, wherein the groove is curved.

13. The device of claim 11, wherein the second hollow bulb further comprises an axis and the curve is at least partially helical around the axis.

14. A device for dispensing fluids, the device comprising:
    a compressible first hollow bulb, the first hollow bulb including a fill port in a side of the first hollow bulb for injecting liquid into the first hollow bulb, the fill port comprising an X-shaped cut covering a portion of the fill port, the X-shaped cut allowing for a liquid-containing nozzle to insert into the port such that the X-shaped cut depresses toward the interior of the of the first hollow bulb, the X-shaped cut returning to a non-depressed form after the liquid-containing nozzle is removed; the X-shaped cut not providing a full seal to the interior of the hollow bulb, but wherein a finger extending over the port provides a substantially-complete seal during compression of the first hollow bulb;
    a second hollow bulb, the second hollow bulb having a hollow interior and comprising a tapered profile, further including a vent along the exterior of the second hollow bulb, the vent extending from near a first end of the second hollow bulb to a second end of the second hollow bulb, the vent comprising a recess in the second bulb allowing for air to pass out of an inner ear when liquid is injected into an ear by compression of the first hollow bulb;

a gap between the first hollow bulb and the second hollow bulb; the gap less than the length of first hollow bulb and second hollow bulb; and a stem coupling the first hollow bulb and the second hollow bulb, the stem providing fluid flow between the first hollow bulb and the second hollow bulb;

wherein the stem allows for bending of the first and second bulbs relative to one another such that the first hollow bulb is substantially vertical and the second hollow bulb is substantially horizontal; and wherein fluid travelling through the second hollow bulb only travels through the conduit and does not otherwise enter the hollow interior of the second hollow bulb.

* * * * *